United States Patent
Questa et al.

(10) Patent No.: US 11,633,175 B2
(45) Date of Patent: Apr. 25, 2023

(54) METHOD AND ULTRASOUND SYSTEM FOR SHEAR WAVE ELASTICITY IMAGING

(71) Applicant: ESAOTE SpA, Genoa (IT)

(72) Inventors: Antonio Questa, Novi Ligure (IT); Davide Carlini, Genoa (IT); Giovanni Bini, Genoa (IT); Marco Crocco, Ovada (IT)

(73) Assignee: Esaote S.p.A., Genoa (IT)

( * ) Notice: Subject to any disclaimer, the term of this patent is extended or adjusted under 35 U.S.C. 154(b) by 725 days.

(21) Appl. No.: 16/381,462

(22) Filed: Apr. 11, 2019

(65) Prior Publication Data

US 2019/0328364 A1    Oct. 31, 2019

(30) Foreign Application Priority Data

Apr. 30, 2018  (EP) .................................... 18170035

(51) Int. Cl.
| | |
|---|---|
| *A61B 8/14* | (2006.01) |
| *A61B 8/08* | (2006.01) |
| *A61B 8/00* | (2006.01) |
| *G06T 5/20* | (2006.01) |

(52) U.S. Cl.
CPC ................ *A61B 8/485* (2013.01); *A61B 8/14* (2013.01); *A61B 8/461* (2013.01); *A61B 8/488* (2013.01); *A61B 8/5207* (2013.01); *G06T 5/20* (2013.01); *G06T 2207/10132* (2013.01)

(58) Field of Classification Search
None
See application file for complete search history.

(56) References Cited

U.S. PATENT DOCUMENTS

| | | |
|---|---|---|
| 5,606,971 A | 3/1997 | Sarvazyan |
| 8,137,272 B2 | 3/2012 | Cooley et al. |
| 2002/0010398 A1 | 1/2002 | Bonnefous |
| 2015/0164480 A1 | 6/2015 | Masaki |
| 2015/0173720 A1 | 6/2015 | Yoshikawa |
| 2017/0156700 A1 | 6/2017 | Honjo |

FOREIGN PATENT DOCUMENTS

| | | |
|---|---|---|
| EP | 3263036 A1 | 1/2018 |
| EP | 3240484 B1 | 3/2019 |
| WO | 2016108178 A1 | 7/2016 |

OTHER PUBLICATIONS

European Search Report dated Aug. 29, 2018, which issued in the corresponding European Patent Application No. 18170035.2.

*Primary Examiner* — Colin T. Sakamoto
(74) *Attorney, Agent, or Firm* — Dickinson Wright PLLC

(57) ABSTRACT

A method for two-dimensional sheare wave elastography imaging comprises: a) acquiring B-mode ultrasound images of a target region in a body; b) selecting a region of interest inside the B-mode image; c) transmitting a shear wave excitation pulse focalized on an excitation region; d) measuring displacements of tracking focal points at different depths positions along laterally staggered tracking lines within the region of interest; e) determining elasticity parameters of the regions between two of the tracking focal points at the same depth and on at least two adjacent tracking lines as a function of the displacements caused by the shear wave at the tracking focal points; f) modifying the appearance of pixel(s) of the B-mode image inside the regions relatively to the grey-scale B-mode image as a function of elasticity parameters determined for the regions; and g) displaying the pixel(s) having a modified appearance at the corresponding pixel of the B-mode image.

32 Claims, 11 Drawing Sheets

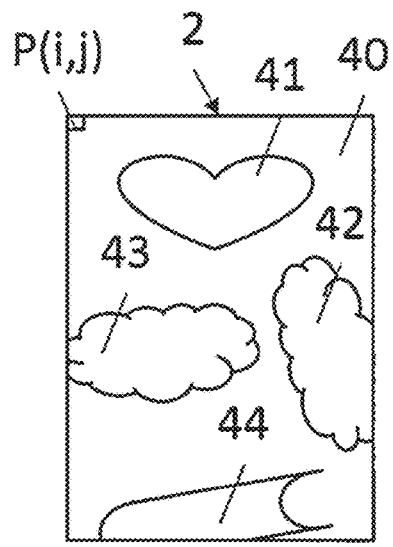 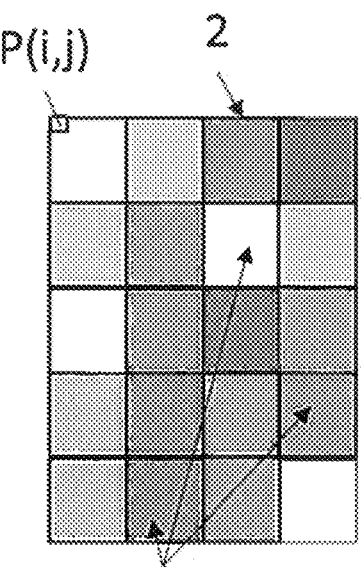 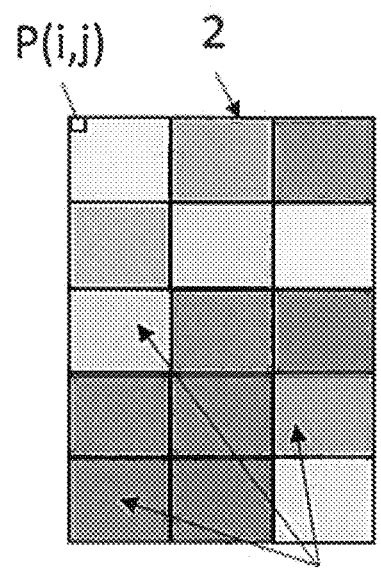
Figure 4A    Figure 4B    Figure 4C
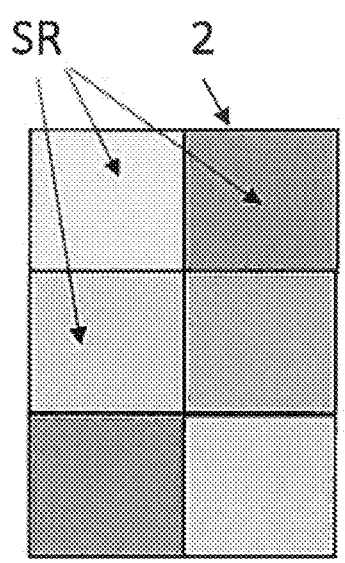 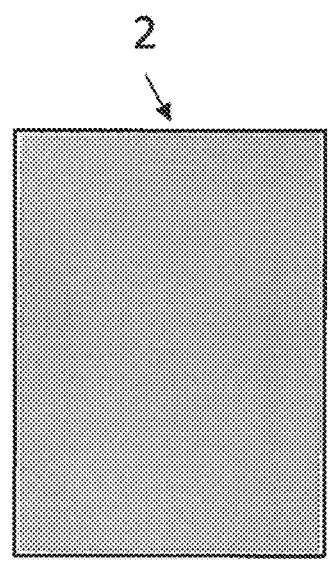
Figure 4D    Figure 4E

METHOD AND ULTRASOUND SYSTEM FOR SHEAR WAVE ELASTICITY IMAGING

BACKGROUND OF THE INVENTION

Elasticity of soft biological tissues has been used for evaluating possible pathological conditions since the dawning of medicine. The use of manual palpations for evaluating the health condition of the tissues is still used commonly in routine medical examinations. For example, the presence of rigid masses found during routine breast examinations is often an early indication of beast cancer. Manual palpation methods however are relatively little objective and are limited to surface anatomical structures.

The methods for quantifying the elasticity or for the comparative measurement of biological tissues by ultrasounds allow deep-tissue elasticity to be measured in the body under examination, are reliable and therefore are used in clinical practice.

Unlike the traditional ultrasound imaging, such as for example B-mode, that allows images to be acquired where tissues with different acoustic properties are distinguished, the methods measuring the elasticity allow tissues with different mechanical properties to be distinguished. To do this, such methods carry out an excitation of the tissues and monitor the strain response, which is related to tissue elasticity.

A type of elasticity measurement methods provides to use transverse waves, or shear waves, generated after an excitation, and are defined as Shear Wave Elasticity Imaging (SWEI). These methods provide to generate shear waves in the tissue following an acoustic disturbance, called as shock disturbance, of the first excitation point applied by the ultrasound probe, and consequently to monitor the shear waves in the regions of interest within an area along which the shear waves propagate. By measuring the displacements over time of the image or of the pixels of the image or of the pixels of a Line of Sight at a plurality of lateral positions separated by a known distance from the excitation source, it is possible to estimate the shear wave speed.

Monitoring the shear waves is carried out by tracking pulses transmitted in the region of interest and the corresponding reflected echoes measures the displacements of the tissues along the at which the tracking pulses are focussed.

The target region at which the excitation pulse of the shear wave is directed is in many cases outside the region of interest within which the monitoring of the shear waves propagation is carried out. More generally, the area at which the shear wave is generated could also be an area placed in the region of interest. In this case, there is the need of monitoring the displacements induced by the shear waves in the tissue also in the area at which the excitation has occurred. Furthermore, also if an excitation pulse is directed to an area outside the region of interest in which the monitoring of the displacements caused by the propagation of the shear wave is carried out, due to an azimuthal translation of a further excitation pulse in relation to the previous ones they said excitation pulse could overlap the region in which one or more tracking pulses of one of the shear wave caused by one of the said previous tracking pulses are transmitted.

Presently, the measurement is indirect since the method detects the propagation speed of the shear wave in a direction substantially orthogonal to the acoustic shock disturbance of the excitation point.

The relation between speed of such shear wave and the elasticity is approximate and it depends on some assumptions about the density of the tissue under examination.

The tissue elasticity is proportional to the propagation speed of the shear wave Vs, according to the following formula:

$$E \mathrel{RS} 3\rho V_s^2$$

Wherein $\rho$ is the density of the tissue and it is assumed that $\rho \mathrel{RS} 1$, namely that tissue density is unitary.

The document U.S. Pat. No. 5,606,971 describes a SWE method that uses a focused ultrasound transducer that induces shear waves in a tissue by sending modulated ultrasonic pulses. The shear wave of the frequency of the modulating signal is detected. The mechanical properties of tissues under examination are evaluated based on the measured values of speed and attenuation of shear waves.

In shear wave elastography, one or a time sequence of shear wave excitation pulses are transmitted to a body to be examined to an excitation target region, which lies outside a selected Region of Interest (ROI) in which the measurement of the elasticity is aimed. The generated shear waves propagate away from the excitation target region or excitation focal point in a direction substantially perpendicular to the direction of transmission of the excitation pulses. The propagation in time of the shear wave is tracked by a series of tracking pulses interleaved to the excitation pulses of the shear waves. Due to the effect of the acoustic radiation force of the excitation pulses, the tissue in the excitation target region is displaced simultaneously establishing a shear wave. For each lateral position along the shear wave propagation direction, which is a direction perpendicular to the excitation pulse, the tissue motion induced by the shear wave will be mainly in the same direction as the one caused by the excitation pulse. Tracking pulses along several laterally staggered focal lines passing through a selected ROI can monitor such dynamic response for selected positions and lead to determining a position-specific displacement waveform representing the magnitude of tissue movement as a function of time caused by the transit of the shear wave front. Such waveforms can be computed at multiple positions along the shear wave propagation path and are processed for determining the speed of the propagation of the shear wave. Several methods have been used for processing shear wave ultrasound tracking data such as for example, Fourier transform for estimating shear wave phase velocity or shear wave amplitude peak-to-peak spatial and temporal calculations for determining shear wave propagation speed. The speed at which a shear wave propagates inside the tissue is determined by the shear modulus, shear viscosity, tissue density and shear wave frequency through some mechanical models. The stiffer the tissue is, the faster the waves move.

In an embodiment, the excitation pulses of the shear waves are transmitted in a direction, which is parallel to a depth direction inside a body to be examined, and the shear wave propagation direction is perpendicular to the said direction. The laterally staggered tracking pulses are also transmitted and received along focalisation lines, which are parallel to the direction of propagation of the said excitation pulses. Since shear waves have a certain width in the direction of propagation of the excitation pulses and in the specific embodiment in the depth direction inside the body to be examined, tracking data is acquired at different positions having different depths along each tracking line. In one dimensional shear wave elastography imaging the data at the different depth positions and along each tracking line are averaged in order to reconstruct the waveform of the displacements as a function of time along the each of the laterally staggered tracking lines. An example of such method is disclosed in document EP3240484.

Two-dimensional (2D) shear wave elastography presents 2D quantitative shear elasticity maps of tissue, which are clinically useful for both focal lesion detection and diffuse disease diagnosis. In this case, the positional data of different tracking focal points having different depth positions along each tracking line are processed separately for each depth position along the said tracking lines. A waveform of the displacement in time is thus generated for every tracking line and for every tracking focal point at a different depth along the tracking lines. The said tracking focal point are inside the area defined by a selected ROI and within the depth range corresponding to the width in the depth direction of the shear wave. In US2002/0010390, a technique according to the two-dimensional shear wave elastography imaging method is disclosed.

As it is disclosed also in document EP3240484, shear wave elastography imaging is carried out in parallel or interleaved with ultrasound morphologic imaging, so called B-mode imaging reproducing the anatomy of an area of the object to be examined. The shear wave elastography imaging is then applied to a selected sub-area, a so-called Region of Interest (ROI) of the B-mode imaged area. The anatomic images allow identifying one or more specific ROI in which shear wave elastography imaging has to be carried out.

SUMMARY OF THE INVENTION

An object consists in providing more precise and direct visual instruments for the physicians in order to correlate the results about the elastic features of the tissue in an imaged ROI and the anatomical structures present in the said ROI as revealed by the B-mode image.

A further object consists in visually differentiating the different parameters which describes the elastic properties of the tissue in the ROI subjected to shear wave elastography imaging by allowing the doctor to directly appreciate the conditions at a certain structure within the tissue imaged and thereby furnishing a more effective and intuitive aid to the diagnosis.

According to embodiments herein, there is a method for two-dimensional shear wave elastography comprising:

a) acquiring B-mode ultrasound images of a target region in a body under examination;

b) selecting a region of interest inside the said B-mode image;

c) transmitting a shear wave excitation pulse focalized on an excitation region;

d) measuring the displacements of a certain number of tracking focal points at different depths positions along each one of a predefined number of laterally staggered tracking lines within the selected region of interest;

e) determining the elasticity parameters of the regions between at least two of the said tracking focal points at the same depth and on at least two adjacent tracking lines as a function of the displacements of caused by the shear wave at the said tracking focal points;

f) modifying the appearance of at least one pixel of the B-mode image inside the said regions relatively to the grey-scale B-mode image as a function of at least one of the elasticity parameters determined for the said regions;

g) displaying the said at least one pixel having a modified appearance at the corresponding pixel of the B-mode image.

In an advantageous configuration, step f) comprises determining pixel appearance in the HSL (Hue, Saturation, Lightness) or the HSV (Hue, Saturation, Value) or the HSI (Hue, Saturation, Intensity) color three space coordinates, particularly the pixel appearance is set by encoding the B-mode intensity value into a first coordinate, the elasticity or velocity parameter into a second coordinate and a fixed value into a third coordinate of the color three space coordinates.

In the coordinate spaces above Hue is the attribute of a visual sensation according to which an area appears to be similar to one of the perceived colours; red, yellow, green, and blue, or to a combination of two of them;

Value, also named Brightness is the attribute of a visual sensation according to which an area appears to emit more or less light;

Lightness and value are the attributes of brightness relative to a brightness of a similarly illuminated white;

Saturation is the attribute defining the colorfulness of a stimulus relative to its own brightness, such as the perceived color of an area appearing to be more or less chromatic.

Intensity is the attribute relating to the irradiated energy and is related to the sensation of more or less brightness or lightness or value according to the above definitions.

The distance of the tracking focal points along each tracking line and the distance of the tracking lines determine the highest resolution, which may extend over only one pixel or over a group of pixels representing a sub area of the region of interest.

As it will appear more clearly in the following description of a detailed embodiment, for determining the elasticity parameters the tissue velocity and thus other elasticity parameters may be calculated as a function of the measured displacements induced by the shear wave at more than two such at three or more adjacent focal points at the same depth on the corresponding tracking lines.

This has the effect that on one side, the calculated elasticity parameters are statistically more reliable but on the other side, the said parameters are averaged for larger sub regions of the region of interest, thereby reducing the resolution.

In relation to the term elasticity parameter according to the present disclosure, such parameter may include one or more of the parameters of the group comprising: velocity of the shear wave propagation, Young's modulus, shear modulus, bulk modulus, Poisson's ratio, Lamè's first parameter, P-wave and combinations of these parameters. This meaning of the term elasticity parameter applies for the description and for the claims.

According to a further improvement, the appearance parameters of the pixels as a function of the calculated elasticity parameters can be a different colour level scale as the grey scale used for displaying the image data in the s-mode image.

The colour scale can be chosen as being a monochromatic scale different as grey, for example red, blue or green or a polychromatic scale.

In one embodiment the appearance of the pixel or the pixels for representing one or more elasticity parameter determined in each sub-region of the region of interest as a function of the measurements at the two or more tracking focal points is monochromatic and the different values of the elasticity parameter are correlated to different shades of one colour.

In one further embodiment the appearance of the pixels for representing the one or more elasticity parameters determined in each sub-region of the region of interest as a function of the measurements at the two or more tracking focal points is polychromatic and the different values of the elasticity parameter are correlated to different colours.

The tracking focal points define a two-dimensional grid of sub regions of the region of interest in which the sub regions have an extension in the direction perpendicular to the tracking lines which is a function of the distance between tracking lines and an extension in the direction of depth, i.e. in the direction of the tracking line which corresponds to the pitch along the tracking lines of the tracking focal points along the tracking line.

When a number n of tracking point is considered for determining the elasticity parameters, the sub region delimited by the first and last tracking line and by the first and last tracking point along the tracking lines in the depth direction determines the area of the sub region. The smallest sub region is delimited laterally by two adjacent tracking lines and in the direction of depth, i.e. of the tracking lines by two adjacent tracking focal points.

According to an embodiment, the B-mode image and the image of the region of interest representing the elasticity parameters in the different sub regions of it are blended in each sub region of the region of interest as a function of the measurements at the two or more tracking focal points, blending is carried out such that the image of the region of interest representing the elasticity parameters and having a different pixel appearance as the B-mode image is displayed overlapped to the B-mode image of the region of interest by applying a transparency factor.

In this case considering to represent the elasticity parameter with a different monochromatic scale of polychromatic scale as the grey level representation of the B-mode image, the coinciding pixels of the image of the B-mode image and of the image representing the elasticity parameters are coloured according to the monochromatic scale or the polychromatic scale used for representing the elasticity parameters but the anatomic structure, for example of a lesion in a region of interest inside a tissue, represented by the grey scale B-mode image still is visible.

According to an embodiment the blending is obtained by determining the appearance of a pixel in the image of a region of interest representing at the same time an part of the anatomic structure and an elasticity parameter of the anatomic structure at the position of the said pixel by a weighted linear combination of the intensity of the pixel according to the grey scale representation of the B-mode image and the intensity of the pixel according to the monochromatic or polychromatic scale representing the elasticity parameter. The weighting factor applied to the intensity of the pixel in relation to the monochromatic or polychromatic scale for representing the elasticity parameters determines the transparency of the elasticity image.

In a further embodiment, the statistical reliability of the elasticity parameters determined as a function of the measured shear wave effects at the different tracking points is determined for the elasticity parameter of each sub-region of the selected region of interest and the pixel appearance is modified in order to visualize also the reliability of the elasticity parameter determined for the corresponding sub-region.

According to an embodiment, the pixel appearance is determined in the HSL (Hue, Saturation, Lightness) or the HSV (Hue, Saturation, Value) or the HSI (Hue, Saturation, Intensity) color three space coordinates, particularly the pixel appearance is set by encoding the B-mode intensity value into a first coordinate, the elasticity or velocity parameter into a second coordinate and the statistical reliability into a third coordinate of the color three space coordinates.

According to an embodiment, the appearance of pixels of the image representing the elasticity parameters represents the value of the elasticity parameter according to a monochromatic or a polychromatic scale different from the grey scale for the pixels in the B-mode image and the statistical reliance of the determined elasticity parameter value is indicated by different value of the saturation of the colour representing the value of the elasticity parameter, the value of the saturation being determined as a function of the statistical reliance of the determined value of the elasticity parameter.

According to an embodiment, which allows to have a rapid interpretation of the reliance data for the different pixels representing the elasticity parameters in the sub regions of the region of interest, a threshold value of a reliance parameter is set and a discrete value of the saturation such as 1 and 0 are set respectively for reliance parameters under or above the said threshold.

Statistical reliance of the elasticity parameters based on the tracking of the shear wave passage at the tracking focal point grid encompassed by the region of interest can be calculated using different statistical methods such as standard deviations, Gaussian curves and other statistical methods for evaluating errors and which are known to the skilled person and lie within a simple choice among the existing methods.

According to embodiments herein, the elasticity or velocity parameter and the B-mode intensity values are visualized as a first image and the statistical reliability of elasticity or velocity parameter and the B-mode intensity are visualized as a second image placed beside the first image.

Other combinations are possible, for example the statistical reliability and the elasticity or velocity parameter may be combined in a single image while the B-mode is displayed as a second image placed besides or three images may be displayed, the first image encoding the elasticity or velocity parameter, the second image being the B-mode image, the third image encoding the reliability parameter or combinations thereof.

In a variant, the elasticity or velocity parameter and the B-mode intensity values of the first single image and the statistical reliability of elasticity or velocity parameter and the B-mode intensity of the second single image are mapped on two of the three coordinates of a color space HSL (Hue, Saturation, Lightness) or the HSV (Hue, Saturation, Value) or the HSI (Hue, Saturation, Intensity), while the third coordinate is set to a constant value.

In another variant, the elasticity or velocity parameter and the statistical reliability of elasticity or velocity parameter are mapped, in a first image, on two of the three coordinates of a color space HSL (Hue, Saturation, Lightness) or the HSV (Hue, Saturation, Value) or the HSI (Hue, Saturation, Intensity), while the third coordinate is set to a constant value; whereas the B-mode image, placed beside the first image, is displayed on a grey scale colormap or monochromatic colormap or polychromatic colormap.

The processing of the shear wave tracking ultrasound signals for determining elasticity parameters of the imaged region of interest can be carried out according to different methods. According to one embodiment, the estimation of the elasticity parameters describing the elasticity features of the imaged region of interest is carried out by estimating the displacements at the tracking focal points and these displacements are used for determining the velocity of the shear wave at each tracking focal point and in a sub-region between at least two adjacent focal points.

Using the estimated shear wave velocity, mechanical properties of the object or subject imaged can be computed. Examples of mechanical properties and related measurement that can be computed include, but are not limited to, shear stress, shear strain, Young's modulus, shear modulus, storage modulus, loss modulus, viscosity, and anisotropy.

Different algorithm may be used for carrying out this operation. According to an embodiment, an autocorrelation algorithm may be employed for determining the said velocity of the shear wave. According to a further embodiment, the velocity of the shear wave can be estimated according to spatial or temporal time-to-peak method. In this method, the shear wave arrival time is estimated at each spatial location defined by a tracking focal point and the shear wave velocity is calculated by a linear regression of those arrival times versus the distance. An embodiment of this method is disclosed in document WO2016/108178 of the same applicant.

The tracking of the shear wave propagation in the region of interest can be carried out according to several methods.

According to a first embodiment the tracking can be carried out by acquiring the ultrasound signals along each one of a certain number of selected tracking lines by focussing a tracking ultrasound pulse along each tracking line and at one or more tracking points at different depths along said line and receiving the reflected signals along the said tracking line from each tracking point at the different depths. The acquisition is carried out one line after the other.

According to a further embodiment the tracking can be carried out by applying a so-called multiline technique such as for example a so-called RTB-beamforming (Retrospective Transmit Beamforming). Examples of this method are disclosed in U.S. Pat. No. 8,137,272 and in EP3263036 of the same applicant.

According to still a further embodiment, the tracking of the shear wave can be carried out by using a method in which an unfocussed plane wave is transmitted into the region of interest and beamforming is carried out during the signal reception phase according to a backpropagation scheme.

In combination with the above mentioned alternative embodiments, for the method of carrying out the shear wave propagation tracking data acquisition several further acquisition techniques known in the art can be used.

Embodiments herein also relate to a method for quantifying the elasticity of a material by ultrasounds comprising:
a) acquiring an ultrasound image;
b) defining a region of interest in the image;
c) defining an excitation region or point in the acquired image lying outside the region of interest;
d) generating at least one acoustic excitation ultrasound pulse and transmitting the said excitation ultrasound pulse focalized at the said excitation region or point, for generating at least one shear wave, which shear wave originates in the first excitation point and has a direction of propagation substantially perpendicular to the direction of propagation of the ultrasound excitation pulse, the said excitation region or point being positioned in such a manner that the shear wave passes through the region of interest;
e) measuring the displacements induced by the shear wave at predefined tracking focal points in the region of interest at a plurality of tracking lines of sight passing through the region of interest and at different predetermined laterally staggered distances from the excitation region or point and within a predefined depth range along each tracking line;
f) calculating the speed of the measured shear wave using the said displacement data at the said tracking focal points;
g) assessing, by calculation, elasticity parameter values of the material in the region of interest based on the measured speed of the shear wave.

According to an embodiment, step g) is carried out by applying the following steps:
g1) defining sub-regions of the region of interest which sub regions are delimited laterally by two of the tracking lines and in the direction of depth by two tracking points having different depth on each of the said two tracking lines and which two points on the first of the said tracking line having equal depth as the two tracking points on the second tracking line;
g2) the said two tracking lines and the said two tracking points being directly adjacent one to the other or one or more tracking line and/or one or more tracking points being provided between the said two tracking lines and the said two tracking points;
g3) calculating the speed of the shear wave in each of the said sub regions of the region of interest using the displacement data at each tracking point on each tracking line delimiting and/or being within the said sub-region;
g4) assessing, by calculation, an elasticity parameter of the material in each of the sub-regions of the region of interest based on the measured speed of the shear wave.

The material in question can be of any type, both non biological type, as in the case of non-destructive testing, and composed of biological tissues.

According to an embodiment the method provides for the following steps:
acquiring an ultrasound anatomic image of a target object such as a so-called B-mode image;
defining a region of interest in the ultrasound image;
generating an acoustic shear wave excitation ultrasound beam directed and/or focused at an excitation region or point, the said acoustic ultrasound beam being configured to produce a shear wave that has a direction of propagation extending laterally from a direction of propagation of the acoustic disturbance ultrasound beam, i.e. along a direction perpendicular to the direction of transmission of the ultrasound excitation beam;
generating ultrasound tracking beams focused along different tracking line of sight which are at different predetermined laterally staggered distances one from the other and from the said excitation region or point;
processing the ultrasound echo signal reflected at different tracking focal points distributed along the said tracking lines for calculating the values of elasticity parameters in the region of interest;
representing the elasticity parameter value distribution in the region of interest by means of an elasticity image the appearance of the pixels of the said elasticity image being determined as a function of the said elasticity parameter;
scaling the said elasticity image to be congruent with the region of interest selected on the anatomic image and combining the elasticity image with the anatomic image of the region of interest;
displaying the said combined images.

According to embodiment herein, an ultrasound system is provided for shear wave elasticity imaging (SWEI) comprising:
An ultrasound probe;
An ultrasound image acquisition section configured to acquire at least ultrasound anatomic images such as B-mode images;

A shear wave excitation pulse generation unit for transmitting said shear wave excitation pulses at a shear wave excitation region or point in a target region;

An ultrasound shear wave tracking section configured to transmit and receive ultrasound tracking beams in a selected region of interest;

A processing unit of the ultrasound received tracking beams, which unit is configured to calculate elasticity parameter values in the selected region of interest;

An image generation unit for graphically representing the elasticity parameter values in the selected region of interest in an elasticity image;

An image combination unit for combining the image elasticity image with the anatomic image of the said selected region of interest.

An image display receiving the image data from the image combination unit and displaying the combined image.

According to an embodiment, the ultrasound system comprises an ultrasound probe;

An ultrasound transmit-wave generator and an ultrasound transmit beamformer;

An ultrasound receive beamformer;

ultrasound receive signals processing unit for generating ultrasound image data;

a shear wave excitation pulse generator and a shear wave beamformer;

a central control unit comprising
a memory storing program instructions;
at least one processor that executes the program instructions to:
define a region of interest in the ultrasound image;
generate an acoustic excitation ultrasound pulse directed at an excitation region or point, the said acoustic excitation ultrasound pulse being configured to produce a shear wave that has a direction of propagation extending laterally from a direction of propagation of the acoustic excitation ultrasound pulse, i.e. along a direction perpendicular to the direction of transmission of the ultrasound excitation pulse;
generate ultrasound tracking beams focused along different tracking lines which are at different predetermined laterally staggered distances one from the other and from the said excitation region or point;
process the ultrasound echo signal reflected at different tracking focal points distributed along the said tracking lines for calculating the values of elasticity parameters in the region of interest;
representing the elasticity parameter value distribution in the region of interest by means of an elasticity image the appearance of the pixels of the said elasticity image being determined as a function of the said elasticity parameter;
scaling the said elasticity image to be congruent with the region of interest selected on the anatomic image and combining the elasticity image with the anatomic image of the region of interest;
an image display receiving the combined images and displaying the said combined images.

In an embodiment, the processor is configured to determine the statistical reliability of the calculated velocity of the elasticity parameter and modify the pixel appearance of the image or the images to visualize also the reliability of the elasticity parameter.

BRIEF DESCRIPTION OF THE DRAWINGS

FIGS. 4A to 4E show the image representing the elasticity parameters according to different choices of application of the regression algorithm for determining the shear wave velocity and therefrom the elasticity parameters.

FIG. 1 shows the image representing schematically the steps of the method according to an embodiment, an anatomic image of a target region 3 is acquired. On the B-mode image 3 the user defines a region of interest 2 through a gate, in which region of interest the tissue elasticity is desired to be indirectly measured.

Figure 1A:
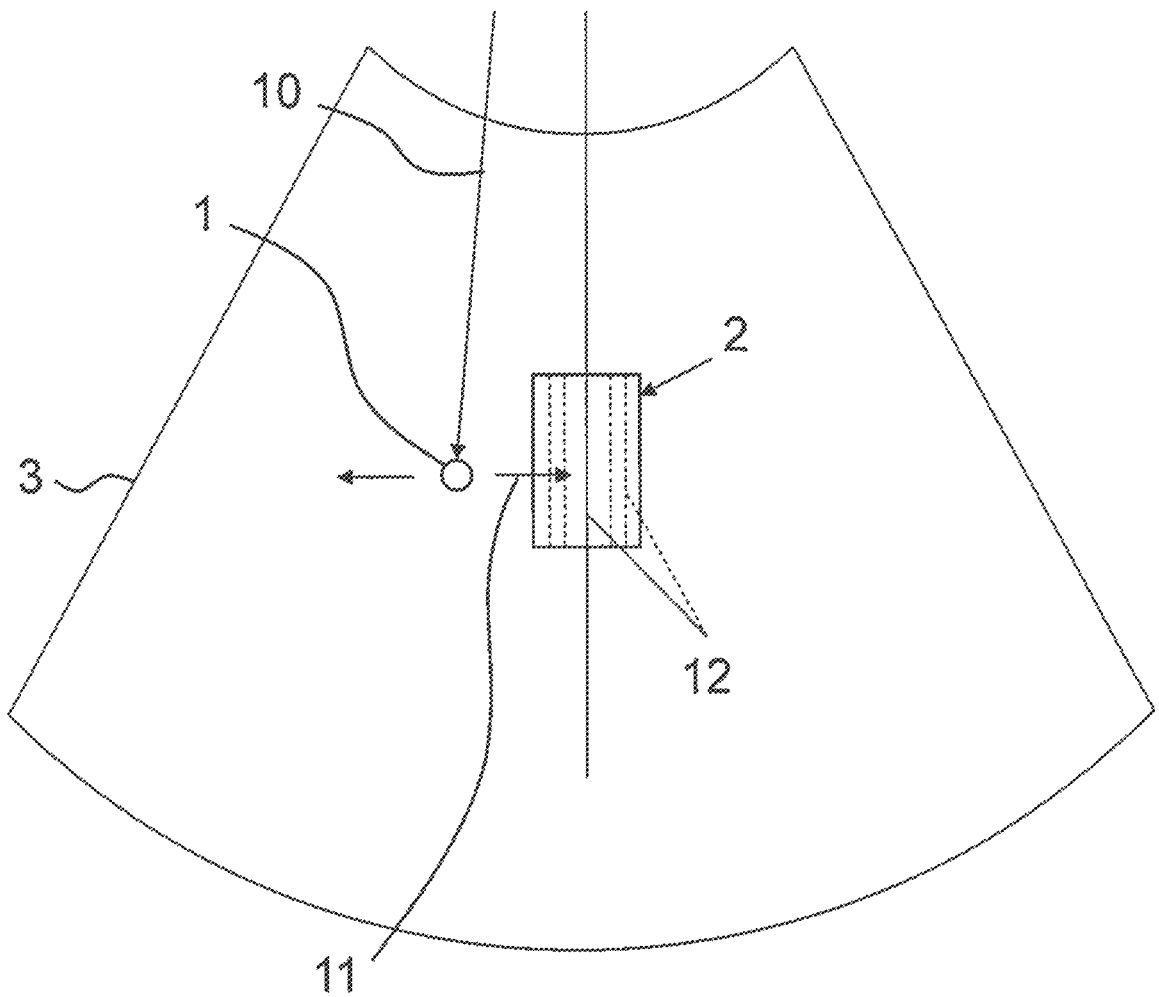
FIG. 1A is a simplified representation of an ultrasound image in which there is shown the region to which the shear wave excitation pulse is applied and the region of interest in which the shear wave propagation is tracked.

The region of interest 2 may have any shape, preferably a rectangular shape or as a section of an annulus, and preferably it has a predetermined size for the end user. The user can place the region of interest 2 where desired.

During the dedicated acquisition, the B-mode image is still, or "frozen", and it can be removed from such condition only after having performed the transmission—reception sequence along the tracking lines which is characteristic of shear wave elastography process.

Once having defined the region of interest 2, the shear wave elasticity imaging process starts. The elasticity parameters of the region of interest are determined by tracking the shear wave passage along the region of interest and as a function of the displacements caused by the shear wave propagation to the material, i.e. the tissue in the region of interest.

Once a measurement has ended, the image can be "unfrozen" such to allow a new shot and a new acquisition, till leaving the mode.

Once the region of interest 2 is defined, an excitation point or region 1 is defined within the acquired B-mode image 3. The excitation point or region is placed outside the region of interest 2 and preferably laterally displaced relatively to the region of interest when referred to the direction of propagation of the tracking beams 12.

Therefore, a focused ultrasonic beam 10 is generated for acoustically generating an excitation pulse at point or region 1, to cause the generation of a shear wave 11. The shear wave 11 originates in the excitation point or region 1 and has a propagation direction substantially perpendicular to the direction of propagation of the ultrasonic excitation beam 10, in the two opposite departing directions denoted by the arrows P in the FIG. 1A. Excitation point 1 is placed such that the shear wave 11 passes through the region of interest 2. The generated shear wave 11 is measured at a plurality of lines of sight 12 which are focused such that they pass inside the region of interest 2 at different predetermined lateral distances from the said excitation point 1. The FIG. 1A shows the line of sight under examination as a continuous line 12, while the other lines of sight are broken lines.

By the measurement of the passage of the shear wave on all the tracking lines or lines of sight 12 the propagation speed of the measured shear wave is calculated.

Figure 1B:
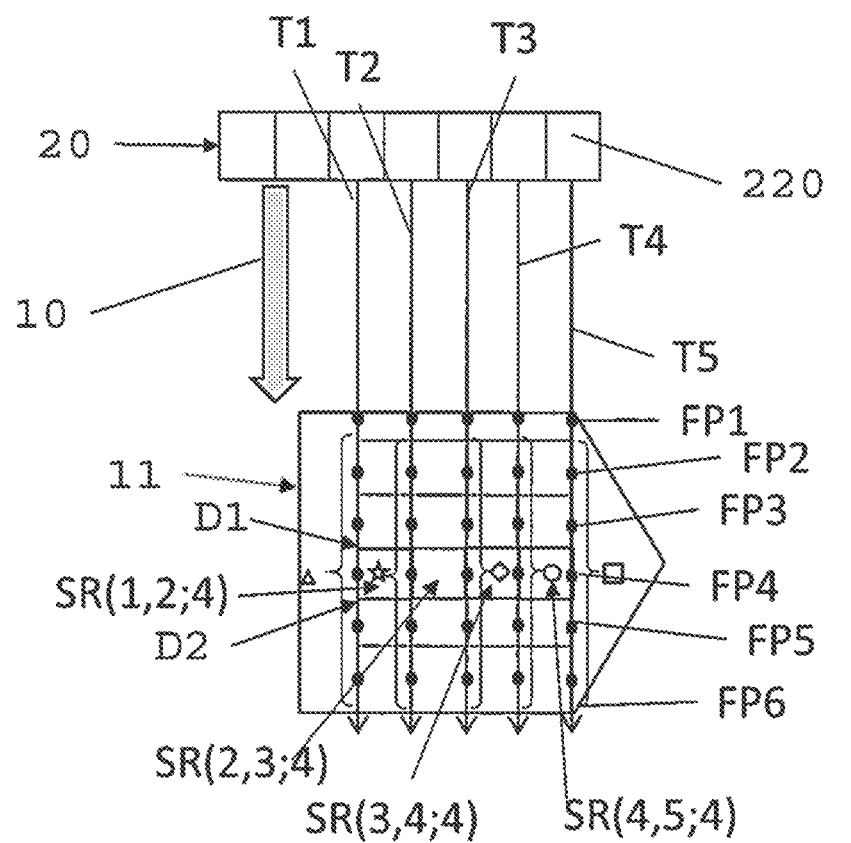
FIG. 1B is a schematic more detailed representation of FIG. 2 in which the shear wave depth range is shown and the tracking focal points along a certain number of tracking lines are represented.

FIG. 1B adds more details to the representation of FIG. 1A.

Here the probe 20 is represented diagrammatically as a linear array of transducers 220. The arrow 10 represents the tracking pulse focused at an excitation point or region along a certain line adjacent to the region of interest. The shear wave 11 is represented by the arrow and has a certain width in the depth direction i.e. in the direction of propagation of the tracking beams T1, T2, T3, T4 and T5 and the direction of propagation of the shear wave is indicated by the arrow like shape. The tracking beams T1 to T5 are focused each one along a line of sight of a plurality of lines of sight which are distributed over the extension of the region of interest. The term lateral means here in the direction of propagation of the shear wave 11.

Along each tracking line the corresponding tracking beam is focused at a certain number of tracking focal points FP1 to FP6 which are positioned at different depth in the region of interest.

Ultrasound tracking beams are repeatedly transmitted focused along the tracking lines and the received data are processed in for determining the displacements of the tissue in the region of interest caused by the propagation of the shear wave.

The displacement is a mean displacement since it is averaged in the space, by grouping the displacement measurement between near pixels. On each tracking line, and at each tracking point along the corresponding tracking line the measurement of the displacement is repeated over time to form a sample curve representing the passage of the shear wave.

According to an embodiment such curve may be filtered by a moving mean such to eliminate noise.

For each tracking line and at each tracking focal point at the different depth the measured curve shows the displacement at the corresponding focal point as a function of time.

According to the present embodiment, the peak of the measured displacement is defined to find the shear wave propagation speed: the peak instant on each line of sight and at each tracking focal point FP1 to FP6 related to the known distance of the lines of sight from each other allows the propagation speed to be calculated.

Identifying the peak is the most simple and advantageous operation, but as an alternative it is possible to consider other significant points of the curve such as for example the maximum slope point or the correlation between the curves or the difference between curves.

According to the above process, the displacements inside the region of interest along each of the tracking lines and at the different depth of the tracking focal points are considered, such to reconstruct the shear wave propagation pattern by the measurement of all the tracking lines and the shear wave speed obtained from the said propagation pattern may be processed for calculating the distribution of the elasticity parameter along the region of interest.

According to an embodiment, the examination may be structured in repeated acquisition sequences, and each sequence comprises the transmission of an acoustic excitation pulse at the excitation point and a measurement of the displacements at the tracking focal points of a single tracking line or of a plurality of tracking lines acquired in parallel.

When the measurement of the displacements induced by the propagation of the shear wave occurs line by line it is necessary to transmit an excitation pulse for each of the measurements on the different lines of sight acquired individually or in parallel.

For example, it is possible to acquire one line of sight a time or two or four lines of sight a time in parallel, with standard B-mode imaging techniques.

Tracking of the displacement data along two or more of the tracking lines can also be carried out in an interleaved manner for the two or more tracking lines relatively to each shear wave generation event after a shear wave excitation pulse of a sequence of excitation pulses.

According to an embodiment, such sequence of excitation pulses has a limited number of excitation pulses transmitted with a certain repetition frequency and each series of excitation pulses is interrupted for a certain period by a cooling period before being carried out again. The B-mode image acquisition and the corresponding image may be frozen for the time during which a series of excitation pulses is being transmitted and the B-mode image may be refreshed by a new image acquisition during the cooling period between the repetition sequences of excitation pulses.

Such feature has also the advantage of allowing hardware to be prepared to perform a new transmission series of excitation pulses, and at the same time of allowing the probe and the tissues to cool.

In a further embodiment, for each tracking line, before the transmission of the shear wave excitation pulse, one or more reference measurements on the line of sight under examination are carried out. Thus, the displacement at each of the tracking points can be measured in relation to a reference condition where the tissue in the region of interest is not disturbed by the passage of the shear wave.

According to a further embodiment, the data detected by the measurement of the shear wave are processed for filtering possible artefacts. Preferably such processing is carried out before the calculation of the displacement on each line of sight and the following calculation of the shear wave propagation speed.

In one embodiment, an ECG signal is recorded and the generation of ultrasound beams and the measurement of the displacement of pixels in the image induced by the shear wave passing through the region of interest are synchronized with the ECG signal.

Thus, the method can perform a triggering on the heartbeat, in order to try to suppress as much as possible the movement-related artefacts, for which the shear wave imaging is very sensitive.

This embodiment can be used for the measurement of the elasticity of any biological tissue involved by the cardiac movement, and it is particularly advantageous in relation to the measurement on the left part of the liver, that is the liver part affected by the heartbeat.

The processing of the acquired data substantially is divided in the following 3 macro-steps:

I. Processing all the repetitions of the acquisition of a line of sight to obtain the extraction of the pattern over time of the displacements of the tissue on such line of sight at each tracking focal point within the region of interest 2;

II. Processing the whole set of results deriving from the previous steps in order to obtain the shear wave speed distribution in the region of interest and out of these data the one or more elasticity parameters in different sub regions of the region of interest III. Generating a graphic representation of the calculated values of the elasticity parameter distribution in the region of interest in the form of an elasticity image by applying to the image pixels representing the corresponding sub region of the region of interest appearance features as a function of the said elasticity parameters.

VI. combining this elasticity image to the anatomical image of the region of interest, i.e. the B-mode image of the region of interest by maintaining the same scaling and the same topological relation of the sub regions in the elasticity image with the anatomical structure in the region of interest.

Figure 2:
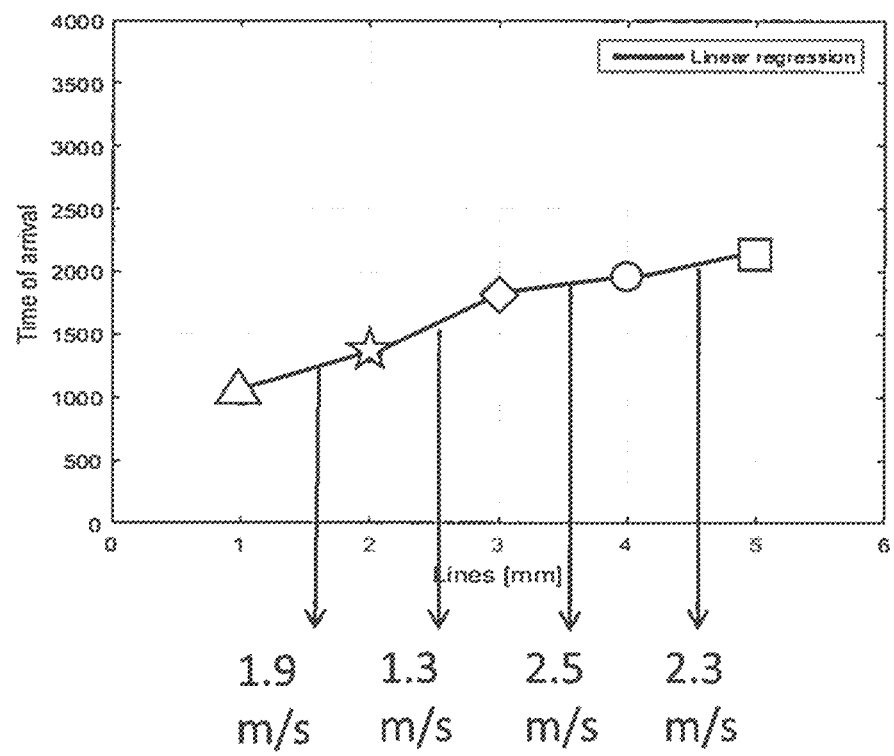
FIG. 2 is the representation of the linear regression method for determining the shear wave velocity in the regions between each pair of two adjacent tracking lines and at a common depth for each of the tracking lines in FIG. 1B.

FIG. 2 shows the result of the linear regression method applied to the time of arrival of the shear wave determined at tracking focal points T(m,n) with m indicating the index of the tracking lines 1 to 5 and n indicating the index of the tracking point at different depth n=1, 2, 3, 4, 5, 6 at the same depth and along a tracking line m. The displacement curves as a function of times at each tracking point of the same depth along the different tracking lines allows to determine a speed value for the shear wave in the said sub-region and to calculate corresponding elasticity parameters. This can be done for each sub region SR(m,m+1; n of the region of interest which sub region is delimited laterally by two adjacent tracking lines T(m), T(m+1) and in the direction of depth by two adjacent lines delimiting a depth range along each tracking line as indicated by D1 and D2 in FIG. 1B. The said depth range is a region centred in depth along each tracking line at a tracking focal point TP(n) on the same tracking line T(m), T(m), T(m+1), T(m+2), . . . , T(m+z), where m is a natural number and having a certain length along the tracking line.

According to the above, in relation to the term tracking focal point, in the present description and in the claims, the meaning of this term shall include the term tracking depth range along a tracking line.

Indeed, after each tracking pulse the reflected data along one or more line of sight are determined. For each line of sight, the RF signal or the data expressed in phase and quadrature deriving from the reflected acoustic tracking beams after the beamforming in reception is distributed over a series of adjacent segments having predefined length along the corresponding line of sight. The segments are representative of a certain depth range along the tracking line. Each segment is considered as representative of a certain depth.

According to an embodiment the depth for which the segment is considered representative coincides with the central point of the segment or with the central sample of the data or signal relating to a corresponding depth range.

According to an embodiment, these segments are cross correlated with analogous segments at the same depth range relating to another tracking pulse which has been emitted before the excitation of the shear wave and having the function of a reference. This operation cross correlating the tracking data in the region of interest before the excitation of the shear wave and after the excitation of the shear wave allows determining the displacement caused by the propagation in the region of interest of the shear wave.

Generalising since other techniques are possible for determining the displacements caused by the shear wave passage in the region of interest out of the reference data and the data after the shear wave excitation, according to a common technique in elastography the displacement is measured by comparing the reference data acquired in the region of interest before the shear wave excitation and the data acquired after the shear wave excitation and during its propagation in the region of interest.

According to one embodiment of the present method and system there is provided the said step of measuring the displacements induced by the shear wave in a region of interest by comparing and more specifically crosscorrealting the tracking data obtained along the one or more tracking lines in an acquisition step before the excitation of the shear wave (reference data) and the tracking data obtained by the acquisitions along the tracking lines after the shear wave excitation.

According to an embodiment adjacent segments may overlap each other for a certain length.

Making use of reference measurements in relation to the above definition of the depth range, the minimum dimension of a pixel or of an image unitary area of the elasticity map along the depth direction is determined as the pitch between a depth segment and the following one considering also an overlap if it is present. The sub-region SR I thus limited laterally by two adjacent tracking lines and centred on a tracking point TP(n).

In FIG. 2 the speed of the shear wave in the sub regions SR(1, 2; 4), SR(2, 3; 4), SR(3, 4; 4), SR(4, 5; 4) is calculated as the linear regression between the displacement peaks determined at the tracking points 3, 4 and on each pair of adjacent tracking lines 1, 2; 2, 3; 3, 4; 4, 5. Examples of speed values determined from the different gradients of the lime passing through the displacement data.

Figure 3A:
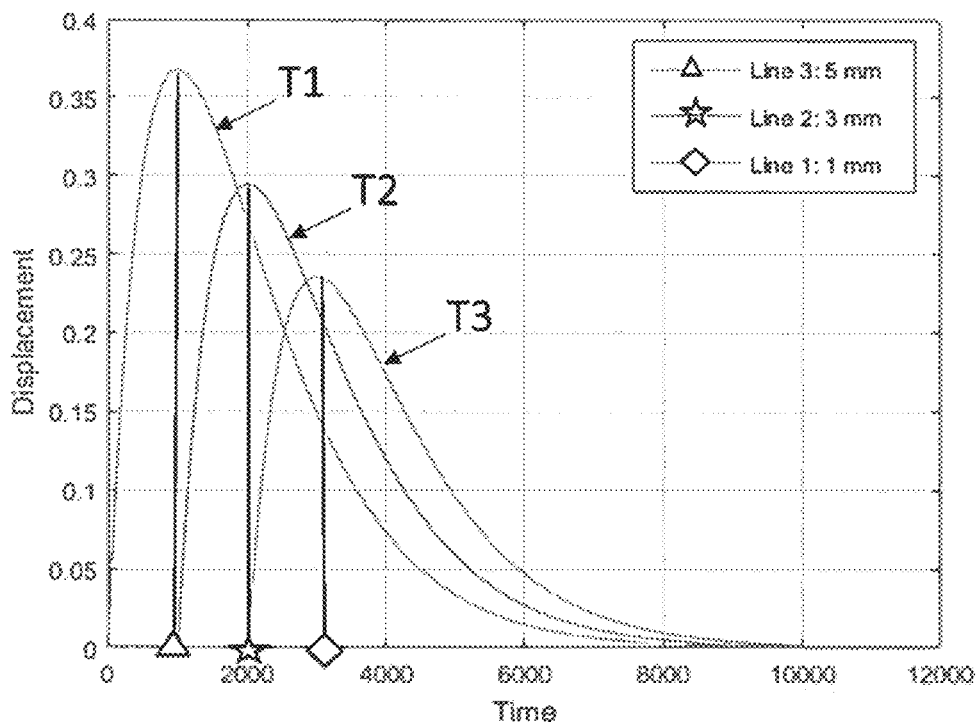
FIG. 3A show a diagram representing the displacement curve as a function of time for each of the first three tracking lines of FIG. 1B.

As indicated in FIG. 3A for only the first three tracking lines, at each tracking point the curve representing the displacement as the function of time. The time of arrival at a certain tracking line is set as the time at which the displacement peak has been measured and the velocity is determined as the gradient of the linear regression of the time of arrival as a function of the tracking line position.

As indicated by the symbols the three curves represent the displacement as a function of time at the first three tracking lines.

Furthermore, the displacement values as a function of time is a mean value of the measured data at the two tracking points delimiting the sub region SR(m,m+1; 4) in the present example.

Figure 3B:
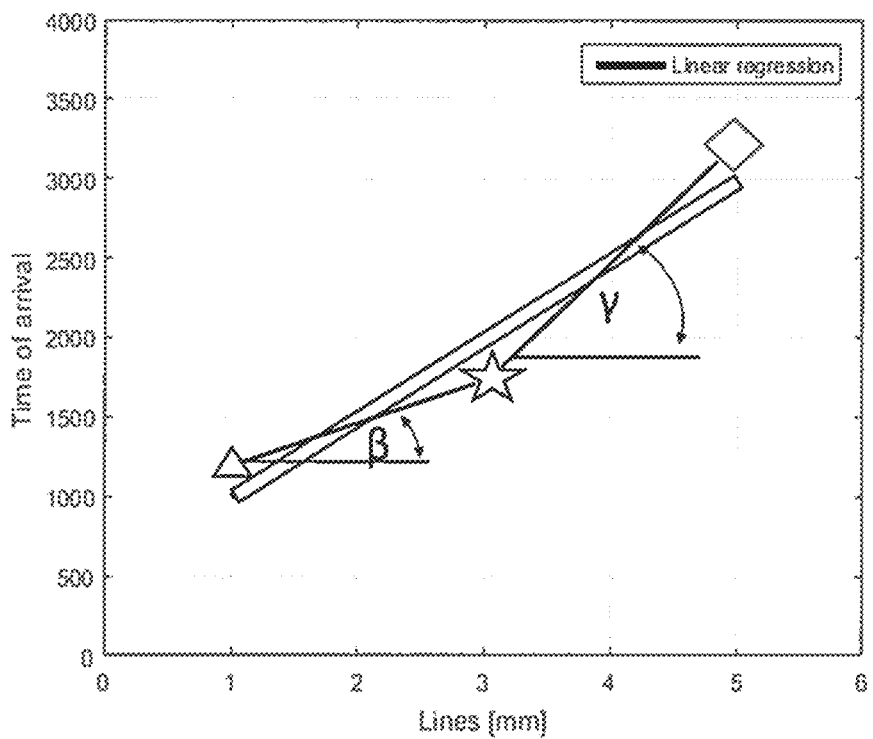
FIGS. 3E and 3C show an example of the regression method for calculating the shear wave velocity at a certain depth according to two different embodiments.

FIG. 3B represents the diagram where the time of arrival is indicated as a function of the three tracking lines T1, T2 and T3 of which the time dependent displacement curves are shown in FIG. 3A. In the case of FIG. 3B the highest resolution of the distribution of elasticity parameters over the region of interest is shown since the region of interest is divided in the smallest possible sub regions determined by the lateral pitch (distance) between adjacent tracking lines and the depth pitch between adjacent tracking points.

The result of the linear regression between the time of arrival respectively on the pair of tracking lines T1 and T2 and T2 and T3 at a certain depth shows that the lines passing through the points have two different inclinations or gradients.

Figure 3C:
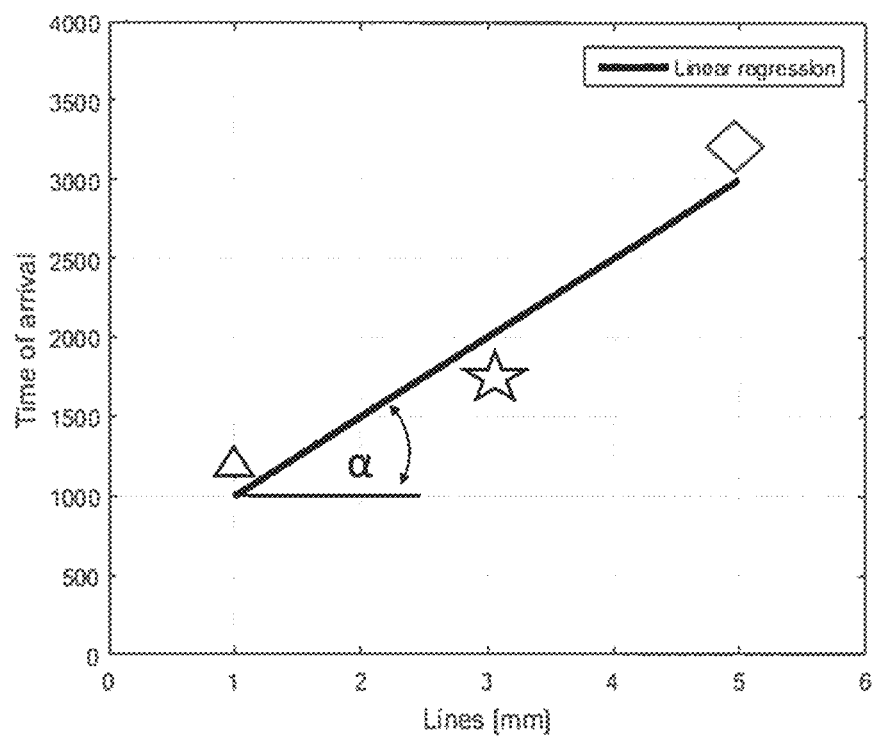

FIG. 3C shows a different choice of determining the velocity distribution in the region of interest which reduces the resolution of the distribution of the velocity data and of the elasticity parameters on the region of interest but reduces the statistical error.

According to the embodiment of FIG. 3C, the sub regions in which the velocity data is calculated are delimited by three tracking lines, which in this case are the three lines T1, T2 and T3. In relation to the dimensions of the sub region in direction of depth the same dimension as in the previous example are considered without any limitation to the fact that the sub regions can have different dimensions in each of the two directions which are independent one from the other. The linear regression is carried out using the determined time of arrivals of the shear wave at each of the three lines and the inclination of the line, i.e. the angle $\alpha$ is different from the angles $\beta$ and $\gamma$ in FIG. 3B.

The following sub region in the image may be calculated by shifting the line triplet by one line so for example the lines used for the calculation of the value in the following sub region will be the lines T2, T3, and T4 and the elasticity parameter of the next sub region will be calculated by using the measurements along the lines T3, T4 and T5 which will also be the last sub region possible since only 5 tracking lines are considered in the present simplified example.

Same way of proceeding may be applied considering the tracking points at different depth, so in the depth direction each sub region may have a dimension corresponding to the region between two adjacent tracking points n, n+1 or between three tracking points or four or five tracking points, similarly to the dimensions of the sub regions in the lateral direction which can be four sub regions having a lateral dimension corresponding to the distance between two adjacent tracking lines or three sub regions having a lateral dimension corresponding to the distance of two tracking lines or two sub regions corresponding to the distance of four tracking lines or only one region corresponding to the lateral dimension of the entire region of interest.

Figure 5A:
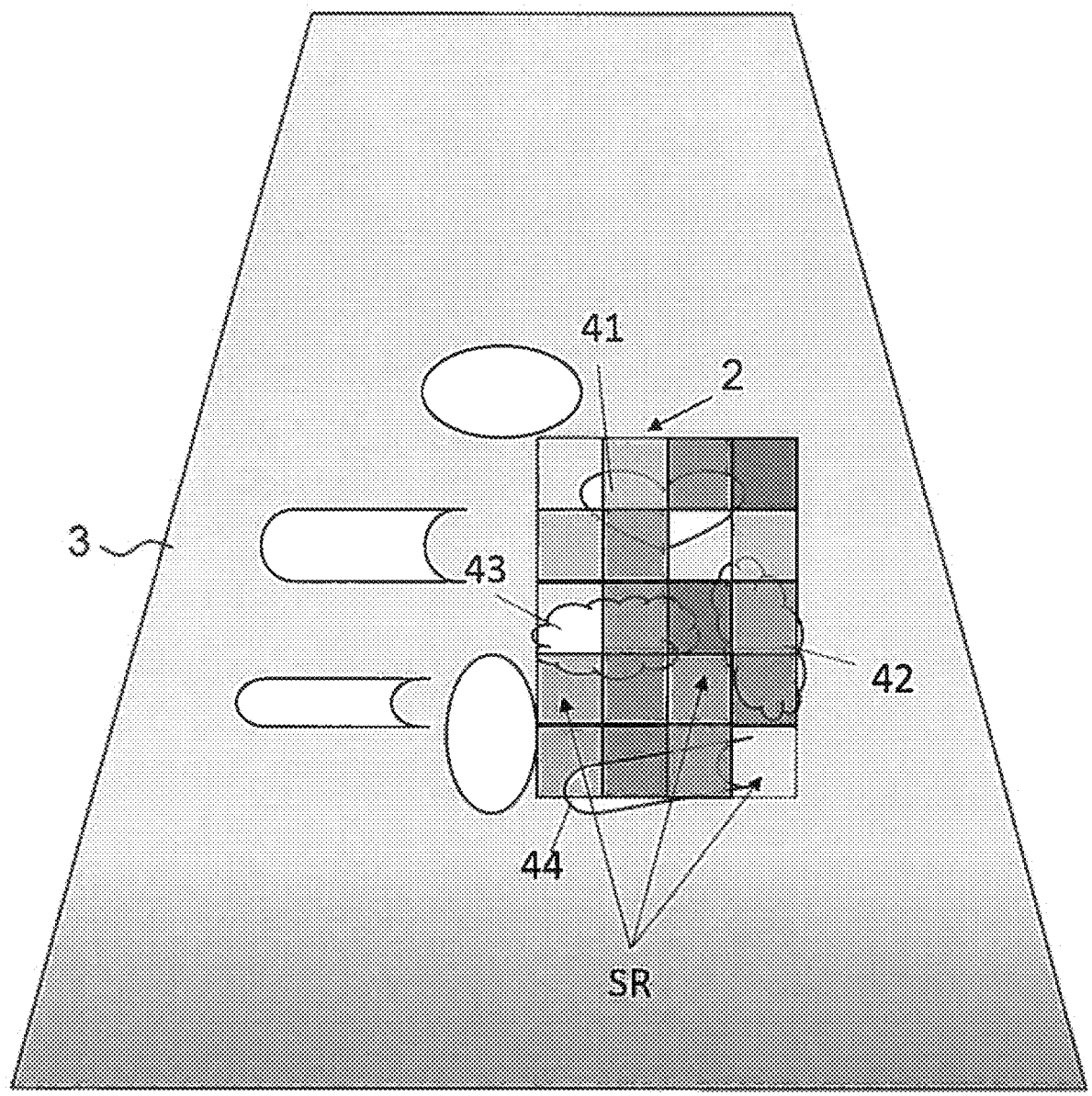
FIGS. 5A and 5B show two schematic representations of a B-mode image in which the image representing the elasticity parameters for the said region of interest is displayed combined with the B-mode image for the pixels of the said region of interest, according to respectively two embodiments related respectively to two different choices of resolutions of the image representing the elasticity parameters.

FIG. 5a shows a diagrammatic example of a region of interest in which different tissues indicated by 40, 41, 42, 43 and 44 are present. FIG. 4B shows an example of a graphic representation of the shear wave elastography imaging in which the values of the shear wave velocity or of the elasticity parameter determined for each sub region SR as defined according to the previous disclosure are represented by a different appearance of the corresponding pixels P(i, j) in the said sub region. In FIG. 4 only one pixel as a sample is shown for clarity sake. The pixel P(i, j) in the elasticity image of FIG. 4B corresponds to the pixel P(i, j) in the B-mode image of the region of interest in FIG. 4A. Normally the B-mode image is represented by modulating the appearance of the image pixels according to a grey scale. The different values of the velocity of the shear wave and/or the corresponding elasticity parameter can be represented by means of a monochromatic scale using a colour different than the grey or by a polychromatic scale. In the present example since colours are not admitted the different values of the velocity of the shear wave or of the corresponding elasticity parameter are represented in a grey scale.

As it appears, the pixels p(i, j) of the B-mode image in the region of interest are modified in relation to their appearance according to a monochromatic different from the grey scale or a polychromatic scale in the image representing the velocity or elasticity data in the different sub regions of the region of interest, maintaining nevertheless the same topological relation to the pixels of the B-mode image.

FIG. 4C shows the elasticity image obtained according to the embodiment of FIG. 3C in which the velocity data is determined by using three lines at the time. Both images 4B and 4C maintains the same dimensions of the sub regions in the depth direction, which is corresponding to the distance of two adjacent tracking points along the tracking lines as indicated in FIG. 1B.

FIG. 4D shows an example of the elasticity image obtained by the present method in which four tracking lines are used for determining the velocity of the shear wave and the corresponding elasticity parameter, while in the direction of depth four tracking points are used and the time dependent curves are obtained by combining the displacement data of four following tracking points of the six available according to FIG. 1B on each tracking line.

FIG. 4E corresponds to the traditional so-called one-dimensional shear wave elastography method in which the displacement curves along each tracking line are determined by combining the measured displacements at every tracking point and the velocity of the shear wave is determined by carrying out the regression by using the maxima of the displacement curves of all the tracking lines.

According to a further embodiment which can be provided alternatively or in combination with the above, the elastic image according to one of more of the examples of FIGS. 4B to 4E can be displayed combined with the B-mode image at least of the region of interest.

According to a first embodiment, the elasticity image can be combined to the B-mode image by displaying the elasticity image overlapped to the B-mode image and with a certain degree of transparency. This can be obtained by weighting the parameters determining the appearance of the corresponding pixel in the image reproducing the shear wave velocity or the elasticity parameter and adding the said weighted parameters to the parameters determining the pixel appearance according to the grey scale in the B-mode image.

According to an embodiment, the pixel appearance parameter is determined according to a HSL or HIS or HSV colour space. In particular, with reference to HSV colour space, the elasticity or velocity parameter can be encoded in the hue (H), while the pixel intensity of B-mode can be encoded in the value (V), whereas the saturation (S) can be set to a constant. This example can be generalized to whatever association between elasticity (or velocity) parameter and B-mode intensity and two of the three colour space coordinates H, S and V. The same holds for HSL space or HSV space.

Figure 5B:
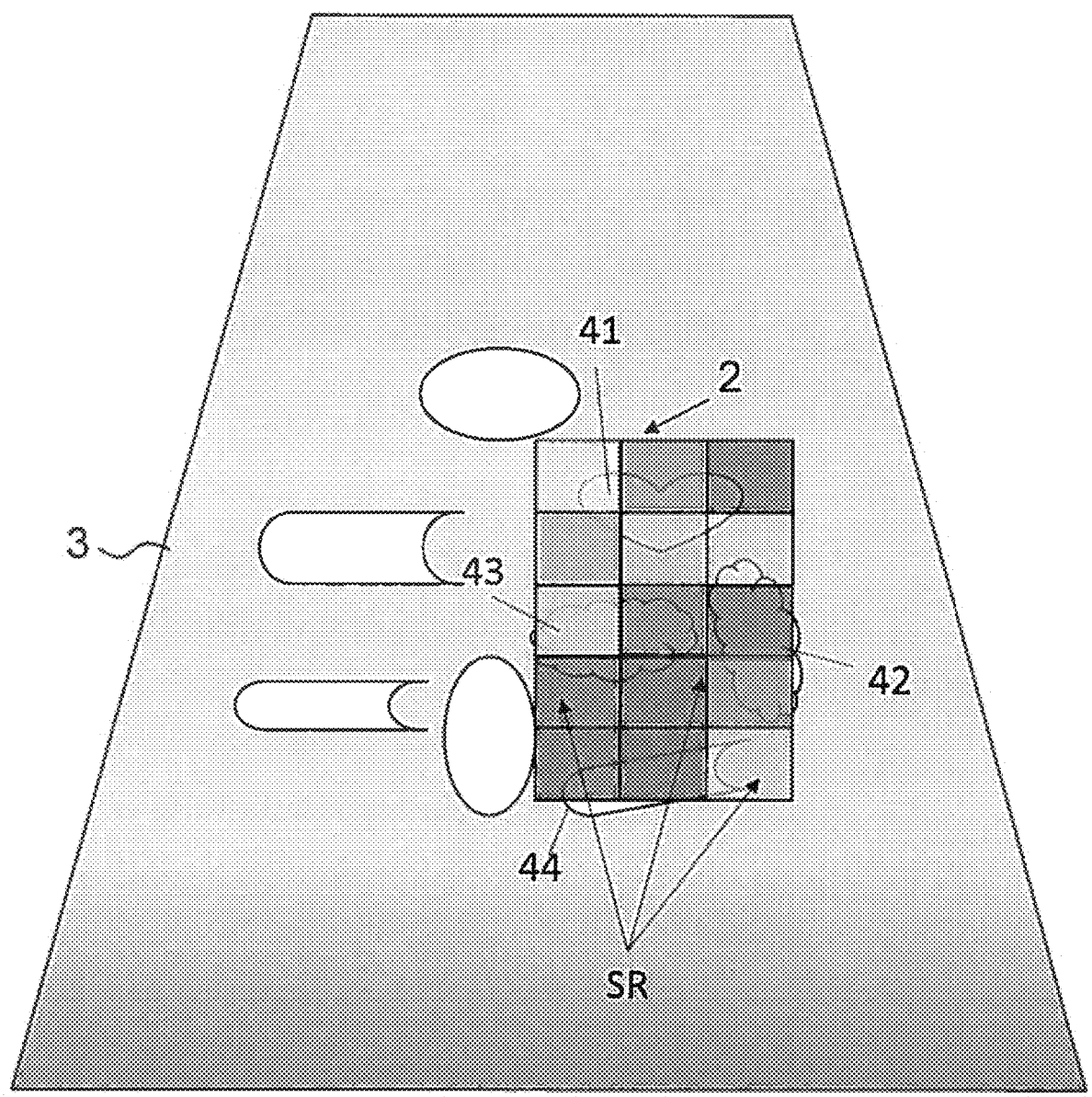

This condition is simulated in FIGS. 5a and 5B for the two different examples of the elasticity image represented in FIGS. 4B and 4C. The B-mode image is encoded in the brightness (value) of each pixel, while the elasticity (or velocity) parameter is encoded in the hue of each subregion. Since the images are in black and white in the present document, the hue is represented as different shades of grey. The different tissues 40 to 44 can be still seen by the user while the corresponding pixels grey shade indicates different values of the corresponding elasticity parameters as calculated from the measured displacements caused by the passage of the shear wave through the region of interest.

According to still a further embodiment, in addition to B-mode intensity levels and elasticity (or velocity) parameter, also the statistical reliability of the estimated elasticity can be graphically displayed in the HSV or HSL or HIS colour spaces. The statistical reliability can be represented by the standard deviation of the error in the linear fitting process or by whatever other parameter representing the statistical fitness of the estimation algorithm. In one embodiment, considering the HSV colour space, the B-mode intensity is encoded in the value (V), the elasticity (or velocity) is encoded in the hue (H) and the statistical reliability is encoded in the saturation (S). In other embodiments whatever association between the triplet H, S, V (or H, S, L or H, I, S) and the triplet B-mode intensity, elasticity (or velocity), reliability can be adopted to display on a single image the B-mode image the elasticity values and their statistical reliability.

In another embodiment, two images are displayed beside each other. In one of the two only the elasticity parameter and its statistical reliability are encoded in a single image, associating to them two of the three colour space coordinates (H, S, V) or (H, S, L) or (H, I, S) and fixing the remaining one to a constant level. In the other image only the intensity values of B-mode are displayed in standard grayscale.

In another embodiment, two images are displayed beside each other. In one of the two, the pixel intensities related to B-mode and the elasticity (or velocity) parameter are encoded associating to them two of the three colour space coordinates (H, S, V) or (H, S, L) or (H, I, S) and fixing the remaining one to a constant level. In the other image the pixel intensities related to B-mode and the statistical reliability of elasticity (or velocity) are encoded associating to them two of the three colour space coordinates (H, S, V) or (H, S, L) or (H, I, S) and fixing the remaining one to a constant level.

Figure 6:
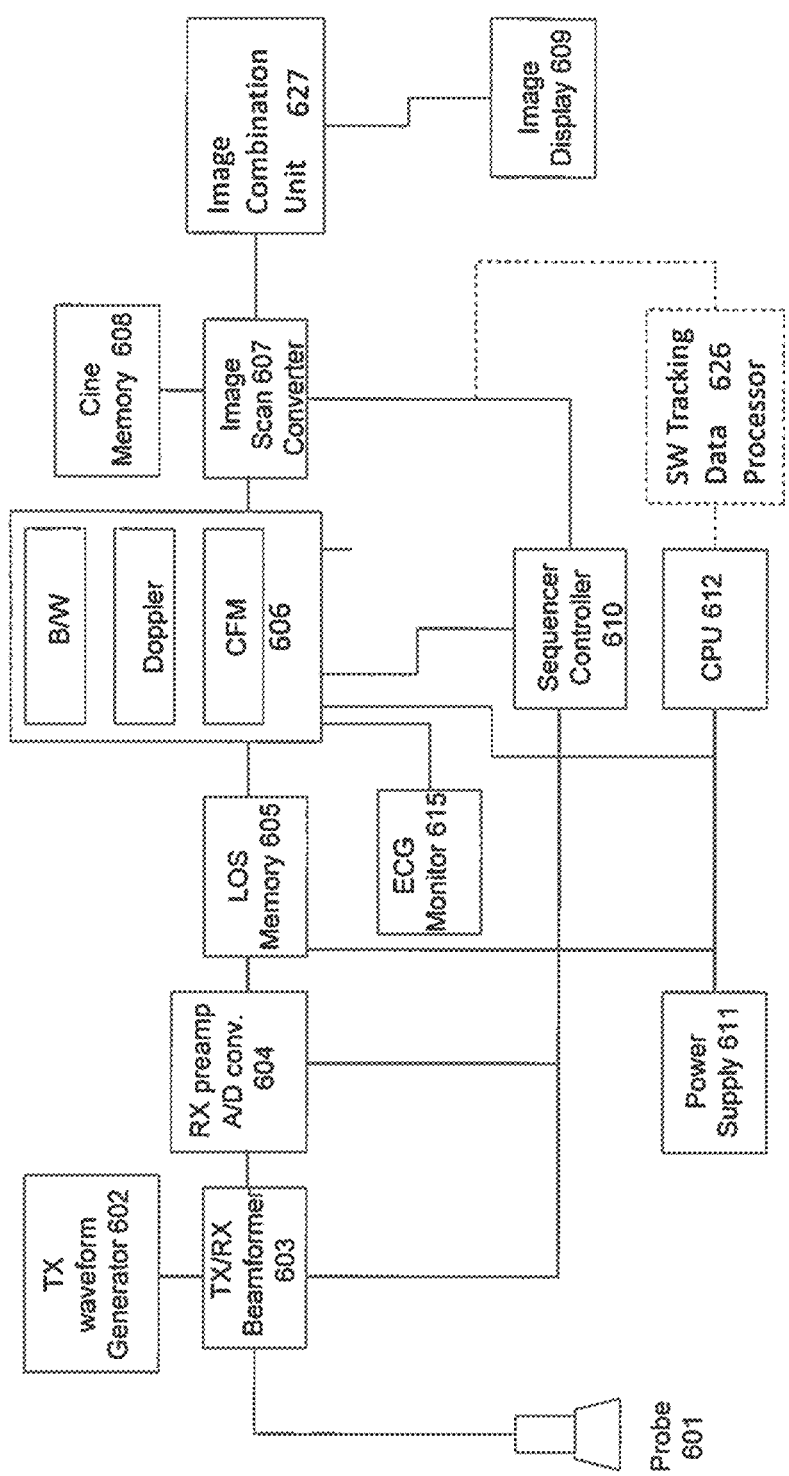
FIG. 6 show a high-level block diagram of an ultrasound system for carrying out shear wave elasticity imaging.

FIG. 6 illustrates a high-level block diagram of an ultrasound system. Portions of the system (as defined by various functional blocks) may be implemented with dedicated hardware, such as transmit/receive (TX/RX) driving/preamp and power switching circuitry, which may utilize analog components. Digital components, DSPs and/or FPGAs, may be utilized to implement the sequencer controller and the timing generator.

The ultrasound system of FIG. 6 includes one or more ultrasound probes 601, 620. The probe 601 may include various transducer array configurations, such as a one-dimensional array, a two-dimensional array, a linear array, a convex array and the like. The transducers of the array may be managed to operate as a 1D array, 1.25D array, 1.5D array, 1.75D array, 2D array, 3D array, 4D array, etc.

The ultrasound probe 601 is coupled over a wired or wireless link to a beamformer 603. The beamformer 603 includes a transmit (TX) beamformer and a receive (RX) beamformer that are jointly represented by TX/RX beamformer 603. The beamformer 603 supplies transmit signals to the probe 601 and performs beamforming of "echo" signals that are received by the probe 601.

A TX waveform generator 602 is coupled to the beamformer 603 and generates the transmit signals that are supplied from the beamformer 603 to the probe 601. The transmit signals may represent various types of ultrasound TX signals such as used in connection with B-mode imaging, colour Doppler imaging, pulse-inversion transmit techniques, contrast-based imaging, M-mode imaging and the like. In accordance with embodiments herein, the transmit signals include acoustic disturbance ultrasound (ACU) beam (10, in FIG. 1A) that are directed at select excitation points or regions (1 in FIG. 1A). The ACU beams are configured to generate shear waves as described herein.

The beamformer 603 performs beamforming upon received echo signals to form beamformed echo signals in connection pixel locations distributed across the region of interest. For example, in accordance with certain embodiments, the transducer elements generate raw analog receive signals that are supplied to the beamformer. The beamformer adjusts the delays to focus the receive signal along a select receive beam and at a select depth within the ROI. The beamformer adjusts the weighting of the receive signals to obtain a desired apodization and profile. The beamformer sums the delayed, weighted receive signals to form RF beamformed signals. The RF beamformed signals are digitized at a select sampling rate by the RX preamp and A/D converter 604. The RF beamformed signals are converted to I, Q data pairs.

The TX waveform generator 902, TX/RX beamformer 603 and A/D converter 604 cooperate to generate the acoustic disturbance ultrasound beams (10) directed at the excitation point (1) The acoustic disturbance ultrasound beams are configured to produce shear waves (11) that have directions of propagation extending laterally from the directions of propagation of the acoustic disturbance ultrasound beams (10). The I, Q data pairs are saved as image pixels in the line of sight (LO) memory. For example, the LOS memory may include LOS memory portions associated with each line of sight through the ROI. The I, Q data pairs, defining the image pixels for corresponding individual ROI locations along a corresponding LOS, are saved in the correspond LOS memory portion. A collection of image pixels (e.g., I, Q data pairs) are collected over time and saved in the LOS memory 605. The image pixels correspond to tissue and other anatomy within the ROI. As the ROI experiences the shear waves, the tissue and other anatomy in the ROI moves in response to the shear waves. The collection of image pixels captures the movement of tissue other anatomy within the ROI.

In embodiments, a dedicated sequencer/timing controller 610 may be programmed to manage acquisition timing which can be generalized as a sequence of firings aimed to locally generate shear waves aside the measurement box followed by tracking firings to monitor transition of the shear waves through the acquisition lines (LOS) in the measurement box (corresponding to the ROI). Optionally, idle phases can be added to control heating of the probe and manage compliance with safety emission regulations.

A sequence controller 610 manages operation of the TX/RX beamformer 603 and the A/D converter 604 in connection with transmitting ADU beams and measuring image pixels at individual LOS locations along the lines of sight. The sequence controller 610 manages collection of reference measurements and shear-wave induced measurements. The sequence controller 610 provides a pause period between a last measurement along one tracking line coincident with one line of sight and a first measurement along a following tracking line coincident with a following line of sight.

One or more processors 606 perform various processing operations as described herein. The CPU 612 may perform one or more of the operations described herein in connection with generation of shear waves, measurement of displacement, calculation of displacement speed, calculation of stiffness values and the like.

Among other things, the processor 606 and/or CPU 612 analyse the image pixels to measure displacement of the image pixels or controls an optional dedicated shear wave tracking data processor 626. The processor 606 and/or the CPU 612 and or the optional shear wave data processor measure the displacement at image pixels for the plurality of lines of sight placed in the region of interest. The lines of sight are located at different predetermined laterally staggered distances from the excitation point (1), (4).

The processor 606 and/or CPU 612 or optionally a dedicated shear wave tracking data processor 626 also calculates a stiffness value based on the speed of the shear wave according to one or more of the examples describe above.

As explained herein, the processor 606 and/or CPU 612 or the dedicated processor 626 obtaining one or more reference measurements for a plurality of lines of sight in the region of interest, prior to generating the first and second shear waves. According to an embodiment, the processor 606 and/or CPU 612 or the optional dedicated processor 626 measure the shear waves (11 include measuring mean displacement over time of the tissue along a plurality of line of sights and identifying a peak of the mean displacements.

For example, the measurements by the processor 606 and/or CPU 612 or the optional dedicated processor 626 may include calculating a cross-correlation between the measurements associated with the shear waves and a reference measurement obtained independent of the shear waves. The processor 606 and/or CPU 612 or the optional dedicated processor 626 measure displacement over time of the tissue along a plurality of line of sights and calculates speeds of the shear waves (11) based, in part, on distances of the corresponding lines of sight from the excitation point (1).

The processor 606 and/or CPU 612 also performs conventional ultrasound operations. For example, the processor 606 executes a B/W module to generate B-mode images. The processor 606 and/or CPU 612 executes a Doppler module to generate Doppler images. The processor executes a Color flow module (CFM) to generate colour flow images. The processor 606 and/or CPU 612 may implement additional ultrasound imaging and measurement operations. Optionally, the processor 606 and/or CPU 612 may filter the displacements to eliminate movement-related artifacts.

An image scan converter 607 performs scan conversion on the image pixels to convert the format of the image pixels from the coordinate system of the ultrasound acquisition signal path (e.g., the beamformer, etc.) and the coordinate system of the display. For example, the scan converter 607 may convert the image pixels from polar coordinates to Cartesian coordinates for image frames.

A cine memory 608 stores a collection of image frames over time. The image frames may be stored formatted in polar coordinates, Cartesian coordinates or another coordinate system.

An image display 609 displays various ultrasound information, such as the image frames and information measured in accordance with embodiments herein. For example, the image display 609 displays the stiffness values, displacement measurements, displacement speeds, and other information calculated in accordance with embodiments herein. The stiffness values, displacement measurements, displacement speeds, and other information may be displayed as image information, as numeric values, graphical information and the like. The display 609 displays the ultrasound image with the region of interest shown. Optionally, the display 609 may display indicia indicating the excitation points (1), where the indicia are overlaid on the ultrasound image and/or presented along opposite sides of the ultrasound image.

Optionally, the system of FIG. 6 may include an ECG monitor 615 that couples an ECG sensor to the patient and records an ECG signal indicative of the patient's heart rate. The processor 606 and/or sequence controller 610 synchronize the generation of acoustic disturbance ultrasound beams (10) and the measurement of the first and second displacements of the image pixels induced by the first and second shear waves (11) with the ECG signal.

The blocks/modules illustrated in FIG. 6 can be implemented with dedicated hardware (DPSs, FPGAs, memories) and/or in software with one or more processors.

A control CPU module 612 is configured to perform various tasks such as implementing the user/interface and overall system configuration/control. In case of fully software implementation of the ultrasound signal path, the processing node usually hosts also the functions of the control CPU.

A power supply circuit 611 is provided to supply power to the various circuits, modules, processors, memory components, and the like. The power front-end may be an A.C. power source and/or a battery power source (e.g., in connection with portable operation).

Optionally, in point Shear Wave acquisition, the RX tracking lines (line of sights—LOSs) may be temporarily stored, either as pure RF or as I/Q data, in the front-end local memories. The processing may be implemented by a dedicated processor module 606 and/or a CPU 612. Processed data, may be formatted as shear wave speed measurements or stiffness values. These, are then added to the ancillary data of the field-of-view under scan and properly reported as an overlay to the image displayed on systems monitor.

According to a further feature, an image combination unit 627 may be present in which the B-mode image data of at least of a region of interest and the corresponding graphic representation as an image of the velocity of the shear wave or of the elasticity parameter determined from said velocity data is combined for the superimposed display of the B-mode image and of the image representing the shear wave velocity and/or the elasticity features determined for the corresponding pixels in the B-mode image. The representation as an image of the velocity or of the corresponding elasticity parameter values and the combination of this image with the B-mode image can be carried out according to one of the previously disclosed methods.

Figure 7:
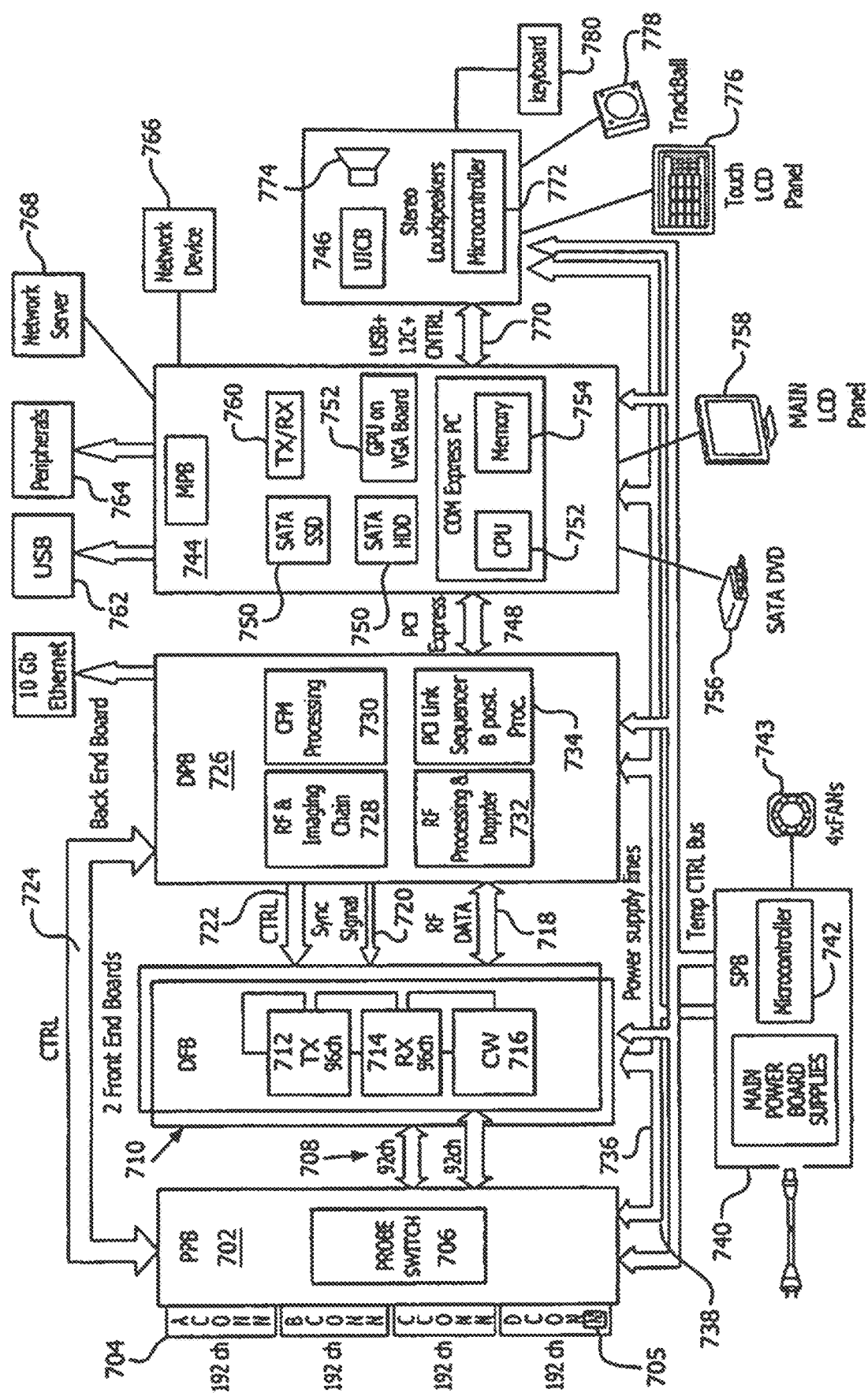
FIG. 7 illustrates a block diagram of an ultrasound system formed in accordance with an alternative embodiment.

FIG. 7 illustrates a block diagram of an ultrasound system formed in accordance with an alternative embodiment. The system of FIG. 7 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynaecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a selected one of the connection ports 704. The connect signal may be generated by the probe when power is initially supplied to the probe when coupled to the connection port 704. Additionally, or alternatively, each connection port 704 may include a sensor 705 that detects when a mating connection on a cable of a probe has been interconnected with the corresponding connection port 704. The sensor 705 provides signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 724. A power supply line 736 provides power from a power supply 740 to the various components of the system, including but not limited to, the probe interconnection board (PIB) 702, digital front-end boards (DFB) 710, digital processing board (DPB) 726, the master processing board (M PB) 744, and a user interface control board (UI CB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally, or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front-end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front-end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front-end boards 716 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front-end boards 710 may convert the RF ultrasound data to I, Q data pairs which are then passed to the digital processing board 726.

The digital processing board 726 includes an RF and imaging module 728, a colour flow processing module 730, an RF processing and Doppler module 732 and a PCI link module 734. The digital processing board 726 performs RF filtering and processing, processing of black and white image information, processing in connection with colour flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728B-734 comprise one or more processors, DSPs, and/or FPGAs, and memory storing program instructions to direct the processors, DSPs, and/or FPGAs to perform various ultrasound image processing operations. The RF and imaging module 728 performs various ultrasound related imaging, such as mode related image processing of the RF data. The RF processing and Doppler module 732 convert incoming RF data to I, Q data pairs, and performs Doppler related processing on the I, Q data pairs. Optionally, the imaging module 728 may perform B mode related image processing upon I, Q data pairs. The CFM processing module 730 performs colour flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 8:
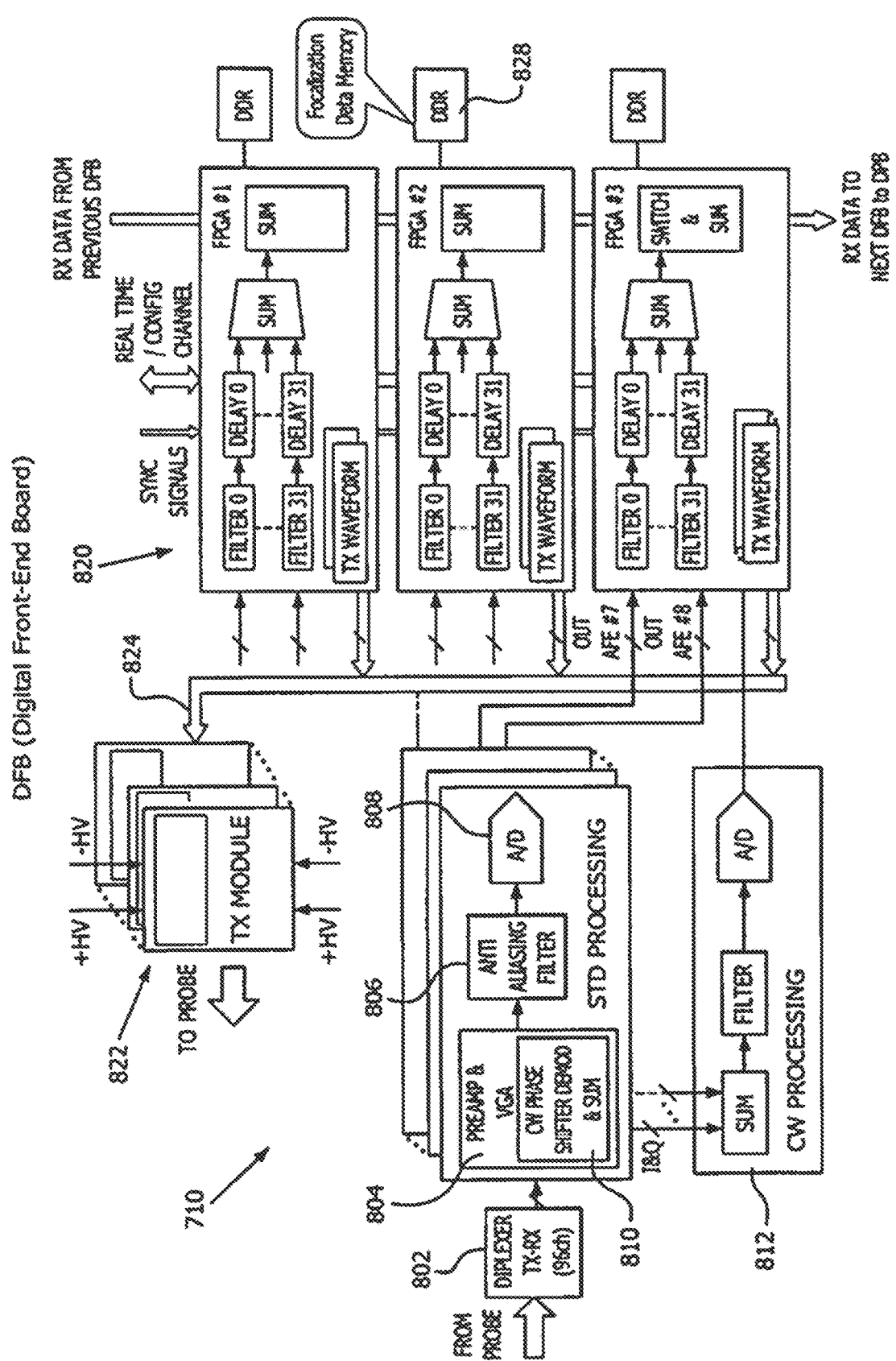
FIG. 8 illustrates a block diagram of a portion of the digital front-end boards.

FIG. 8 illustrates a block diagram of a portion of the digital front-end boards 710 formed in accordance with embodiments herein. A group of diplexers 802 receive the ultrasound signals for the individual channels over the PIB output 808. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti aliasing filter 806 which performs anti-aliasing filtering.

According to an embodiment, the retrospective transmit beam focusing may be applied to the RF data directly acquired by the system or to transformed data according to different transformations as for example as a phase/quadrature (I/Q) transformation, or similar.

In the embodiment of FIG. 8 an example of the said transformation of the RF data is disclosed According to this example, the output of the filter 806 is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I, Q data pairs. The CW I, Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 826 (FIG. 7). The FPGAs receive focalization data from memories 828. The focalization data is utilized to manage the filters, delays and summing operations performed by the FPGAs in connection with beamforming. The beamformed RF or I/Q data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

Figure 9:
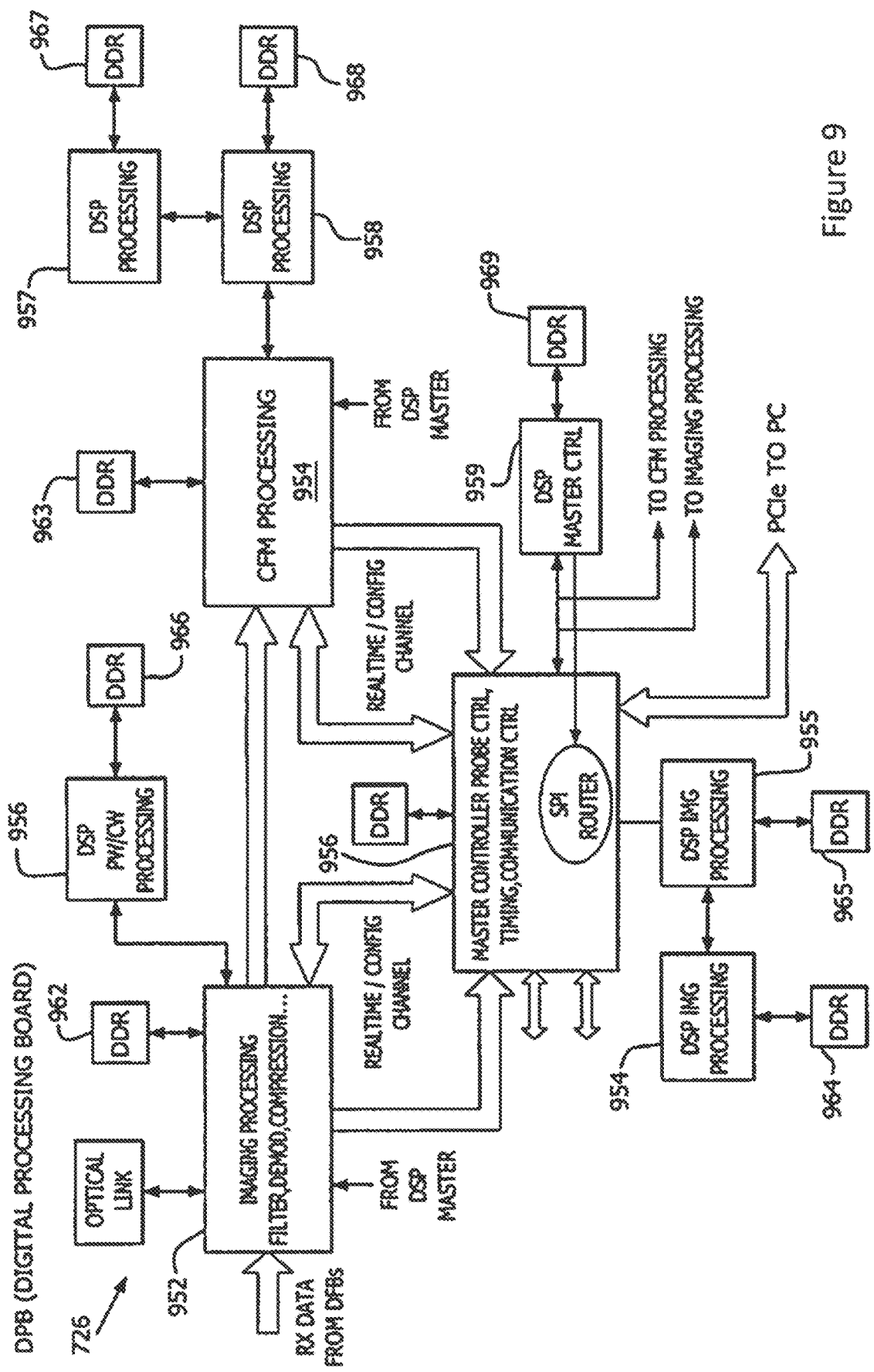
FIG. 9 illustrates a block diagram of the digital processing board.

FIG. 9 illustrates a block diagram of the digital processing board 726 implemented in accordance with embodiments herein. The digital processing board 726 includes various processors 952-959 to perform different operations under the control of program instructions saved within corresponding memories see 952-969. A master controller 950 manages operation of the digital processing board 726 and the processors 952-959. By way of example, one or more processors as the 952 may perform filtering, the modulation, compression and other operations, while another processor 953 performs colour flow processing. The master controller provides probe control signals, timing control signals, communications control and the like. The master controller 950 provides real-time configuration information and synchronization signals in connection with each channel to the digital front-end board 710.

It should be clearly understood that the various arrangements and processes broadly described and illustrated with respect to the FIGS., and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the FIGS., which illustrate example methods, devices and program products according to various example embodiments. These program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally, or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, merle, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e,g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. Method for two-dimensional shear wave elastography imaging comprising:
   a) acquiring B-mode ultrasound images of a target region in a body under examination;
   b) selecting a region of interest inside the said B-mode image;
   c) transmitting a shear wave excitation pulse focalized on an excitation region;
   d) measuring displacements of a certain number of tracking focal points at different depths positions along each one of a predefined number of laterally staggered tracking lines within the selected region of interest;
   e) determining elasticity parameters of regions between at least two of the tracking focal points at the same depth and on at least two adjacent tracking lines as a function of the displacements caused by the shear wave at the tracking focal points;
   f) modifying the appearance of at least one pixel of the B-mode image inside the said regions relatively to the grey-scale B-mode image as a function of at least one of the elasticity parameters determined for the said regions;
   g) displaying the at least one pixel having the modified appearance at the corresponding pixel of the B-mode image;
   wherein a statistical reliability of a calculated velocity or of the elasticity parameter determined as a function of the measured shear wave effects at the different tracking points is determined for the elasticity parameter of each sub-region of the selected region of interest and the pixel appearance is modified in order to visualize also the reliability of the elasticity parameter determined for the corresponding sub-region; and wherein the values of the B-mode image, the elasticity or velocity parameter and the statistical reliability of elasticity or velocity parameter are visualized as a single image by encoding such values in the HSL (Hue, Saturation, Lightness) or the HSV (Hue, Saturation, Value) or the HSI (Hue, Saturation, Intensity) color space.

2. Method according to claim 1, wherein the distance between two adjacent tracking focal points along each of two adjacent tracking lines and the distance between the two adjacent tracking lines determine the highest resolution which may extend over only one pixel or over a group of pixels representing a sub region of the region of interest.

3. Method according to claim 1, wherein the pixel appearance of the pixel or the pixels that represent one or more elasticity parameter determined in each sub-region of the region of interest is displayed as a function of the velocity of the shear wave or of the determined elasticity parameter using a color level scale different from the grey scale used for displaying the image data in the B-mode image.

4. Method according to claim 3, wherein a color scale of the appearance of the pixel or the pixels for representing one or more elasticity parameter determined in each sub-region of the region of interest as a function of the measurements at the two or more tracking focal points is either:
monochromatic, wherein different values of the elasticity parameter are correlated to different shades of one color other than grey, or
polychromatic, wherein the different values of the elasticity parameter are correlated to different colors.

5. Method according to claim 1, wherein the tracking focal points define a two dimensional grid of sub regions of the region of interest in which the sub regions have an extension in the direction perpendicular to the tracking lines which is a function of the distance between tracking lines and an extension in the direction of depth, i.e. in the direction of the tracking line which corresponds to the pitch along the tracking lines of the tracking focal points along the tracking line and in which
when a number n of tracking point is considered for determining the elasticity parameters, the sub region delimited by the first and last tracking line and by the first and last tracking point along the tracking lines in the depth direction determines the area of the sub-region, the smallest sub-region being delimited laterally by two adjacent tracking lines and in the direction of depth, i.e. of the tracking lines by two adjacent tracking focal points.

6. Method according to claim 1, wherein the B-mode image and an image of the region of interest representing the elasticity parameters in the different sub regions of it are blended in each sub-region of the region of interest as a function of the measurements at the two or more tracking focal points such that the image of the region of interest representing the elasticity parameters and having a different pixel appearance as the B-mode image is displayed overlapped to the B-mode image of the region of interest by applying a transparency factor.

7. Method according to claim 1, wherein the elasticity or velocity parameter and the B-mode intensity values are visualized as a first image and the statistical reliability of elasticity or velocity parameter and the B-mode intensity are visualized as a second image placed beside the first image.

8. Method according to claim 7, wherein the elasticity or velocity parameter and the B-mode intensity values of the first single image and the statistical reliability of elasticity or velocity parameter and the B-mode intensity of the second single image are mapped on two of the three coordinates of a color space HSL (Hue, Saturation, Lightness) or the HSV (Hue, Saturation, Value) or the HSI (Hue, Saturation, Intensity), while the third coordinate is set to a constant value.

9. Method according to claim 1, wherein step f) comprises determining pixel appearance in the HSL (Hue, Saturation, Lightness) or the HSV (Hue, Saturation, Value) or the HSI (Hue, Saturation, Intensity) color three space coordinates.

10. Method for two-dimensional shear wave elastography imaging comprising:
a) acquiring B-mode ultrasound images of a target region in a body under examination;
b) selecting a region of interest inside the said B-mode image;
c) transmitting a shear wave excitation pulse focalized on an excitation region;
d) measuring displacements of a certain number of tracking focal points at different depths positions along each one of a predefined number of laterally staggered tracking lines within the selected region of interest;
e) determining elasticity parameters of regions between at least two of the tracking focal points at the same depth and on at least two adjacent tracking lines as a function of the displacements caused by the shear wave at the tracking focal points;
f) modifying the appearance of at least one pixel of the B-mode image inside the said regions relatively to the grey-scale B-mode image as a function of at least one of the elasticity parameters determined for the said regions;
g) displaying the at least one pixel having the modified appearance at the corresponding pixel of the B-mode image;
wherein step f) comprises determining pixel appearance in the HSL (Hue, Saturation, Lightness) or the HSV (Hue, Saturation, Value) or the HSI (Hue, Saturation, Intensity) color three space coordinates; and
wherein the pixel appearance is set by encoding the B-mode intensity value into a first coordinate, the elasticity or velocity parameter into a second coordinate and a fixed value into a third coordinate of the color three space coordinates.

11. Method for two-dimensional shear wave elastography imaging comprising:
a) acquiring B-mode ultrasound images of a target region in a body under examination;
b) selecting a region of interest inside the said B-mode image;
c) transmitting a shear wave excitation pulse focalized on an excitation region;
d) measuring displacements of a certain number of tracking focal points at different depths positions along each one of a predefined number of laterally staggered tracking lines within the selected region of interest;
e) determining elasticity parameters of the regions between at least two of the tracking focal points at the same depth and on at least two adjacent tracking lines as a function of the displacements caused by the shear wave at the said tracking focal points;
f) determining the statistical reliability of the velocity or of the elasticity parameter as calculated;
g) modifying the appearance of at least one pixel of the B-mode image inside the said regions relatively to the grey-scale B-mode image as a function of the elasticity parameter and the statistical reliability of the elasticity parameter;

i) displaying the at least one pixel having the modified appearance at the corresponding pixel of the B-mode image.

12. Method according to claim 11, wherein step g) comprises determining pixel appearance in the HSL (Hue, Saturation, Lightness) or the HSV (Hue, Saturation, Value) or the HSI (Hue, Saturation, Intensity) color three space coordinates.

13. Method according to claim 12, wherein the pixel appearance is set by encoding the B-mode intensity value into a first coordinate, the elasticity or velocity parameter into a second coordinate and the statistical reliability of the elasticity parameter into a third coordinate of the color three space coordinates.

14. Method according to claim 13, wherein the elasticity or velocity parameter is encoded to Hue coordinate, the statistical reliability is encoded to Saturation coordinate and B-mode intensity values are encoded to the remaining color space coordinate.

15. Method according to claim 14, wherein a threshold value of statistical reliability of elasticity or velocity parameter is set and a discrete value of the saturation such as 1 and 0 are set respectively for a statistical reliance factor under and above the said threshold.

16. Method according to claim 11, wherein the elasticity or velocity parameter and the statistical reliability of elasticity or velocity parameter are visualized as a single image and the corresponding B-mode image is visualized as another image placed beside the B-mode image.

17. An ultrasound system for shear wave elasticity imaging (SWEI) comprising:
an ultrasound probe;
an ultrasound transmit wave generator and an ultrasound transmit beamformer to provide transmit signals to the ultrasound probe;
an ultrasound receive-beamformer;
ultrasound receive signals processing unit for generating ultrasound image data from received echo signals;
a shear wave excitation pulse generator and a shear wave beamformer;
an image display;
a memory storing program instructions; and
at least one processor that executes the program instructions to:
a) acquire B-mode ultrasound images of a target region in a body under examination;
b) select a region of interest inside the said B-mode image;
c) transmit a shear wave excitation pulse focalized on an excitation region;
d) measure displacements of a certain number of tracking focal points at different depths positions along each one of a predefined number of laterally staggered tracking lines within the selected region of interest;
e) determine elasticity parameters of regions between at least two of the tracking focal points at the same depth and on at least two adjacent tracking lines as a function of the displacements caused by the shear wave at the tracking focal points;
f) modify the appearance of at least one pixel of the B-mode image inside the said regions relatively to the grey-scale B-mode image as a function of at least one of the elasticity parameters determined for the said regions;

g) display the at least one pixel having the modified appearance at the corresponding pixel of the B-mode image;
wherein a statistical reliability of a calculated velocity or of the elasticity parameter determined as a function of the measured shear wave effects at the different tracking points is determined for the elasticity parameter of each sub-region of the selected region of interest and the pixel appearance is modified in order to visualize also the reliability of the elasticity parameter determined for the corresponding sub-region; and
wherein the values of the B-mode image, the elasticity or velocity parameter and the statistical reliability of elasticity or velocity parameter are visualized as a single image by encoding such values in the HSL (Hue, Saturation, Lightness) or the HSV (Hue, Saturation, Value) or the HSI (Hue, Saturation, Intensity) color space.

18. A system according to claim 17, wherein the at least one processor uses the distance between two adjacent tracking focal points along each of two adjacent tracking lines and the distance between the two adjacent tracking lines to determine the highest resolution which may extend over only one pixel or over a group of pixels representing a sub region of the region of interest.

19. A system according to claim 17, wherein the at least one processor displays the pixel appearance of the pixel or the pixels that represent one or more elasticity parameter determined in each sub-region of the region of interest as a function of the velocity of the shear wave or of the determined elasticity parameter using a color level scale different from the grey scale used for displaying the image data in the B-mode image.

20. A system according to claim 19, wherein the at least one processor uses a color scale of the appearance of the pixel or the pixels for representing one or more elasticity parameter determined in each sub-region of the region of interest as a function of the measurements at the two or more tracking focal points, the color scale being chosen from:
monochromatic, wherein different values of the elasticity parameter are correlated to different shades of one color other than grey, or
polychromatic, wherein the different values of the elasticity parameter are correlated to different colors.

21. A system according to claim 17, wherein the at least one processor uses the tracking focal points to define a two dimensional grid of sub regions of the region of interest in which the sub regions have an extension in the direction perpendicular to the tracking lines which is a function of the distance between tracking lines and an extension in the direction of depth, i.e. in the direction of the tracking line which corresponds to the pitch along the tracking lines of the tracking focal points along the tracking line and in which
when the at least one processor considers a number n of tracking point for determining the elasticity parameters, the sub region delimited by the first and last tracking line and by the first and last tracking point along the tracking lines in the depth direction determines the area of the sub-region, the smallest sub-region being delimited laterally by two adjacent tracking lines and in the direction of depth, i.e. of the tracking lines by two adjacent tracking focal points.

22. A system according to claim 17, wherein the at least one processor blends the B-mode image and an image of the region of interest representing the elasticity parameters in the different sub regions of it in each sub-region of the region of interest as a function of the measurements at the two or more tracking focal points such that the image of the region of interest represents the elasticity parameters and has a different pixel appearance as the B-mode image is displayed overlapped to the B-mode image of the region of interest by applying a transparency factor.

23. A system according to claim 17, wherein the at least one processor operates the image display such that the elasticity or velocity parameter and the B-mode intensity values are visualized as a first image and the statistical reliability of elasticity or velocity parameter and the B-mode intensity are visualized as a second image placed beside the first image.

24. A system according to claim 23, wherein the at least one processor maps the elasticity or velocity parameter and the B-mode intensity values of the first single image and the statistical reliability of elasticity or velocity parameter and the B-mode intensity of the second single image on two of the three coordinates of a color space HSL (Hue, Saturation, Lightness) or the HSV (Hue, Saturation, Value) or the HSI (Hue, Saturation, Intensity), while the at least one processor sets the third coordinate to a constant value.

25. A system according to claim 17, wherein when the at least one processor performs step f), the at least one processor determines pixel appearance in the HSL (Hue, Saturation, Lightness) or the HSV (Hue, Saturation, Value) or the HSI (Hue, Saturation, Intensity) color three space coordinates.

26. An ultrasound system for shear wave elasticity imaging (SWEI) comprising:
an ultrasound probe;
an ultrasound transmit wave generator and an ultrasound transmit beamformer to provide transmit signals to the ultrasound probe;
an ultrasound receive-beamformer;
ultrasound receive signals processing unit for generating ultrasound image data from received echo signals;
a shear wave excitation pulse generator and a shear wave beamformer;
an image display;
a memory storing program instructions; and
at least one processor that executes the program instructions to:
a) acquire B-mode ultrasound images of a target region in a body under examination;
b) select a region of interest inside the said B-mode image;
c) transmit a shear wave excitation pulse focalized on an excitation region;
d) measure displacements of a certain number of tracking focal points at different depths positions along each one of a predefined number of laterally staggered tracking lines within the selected region of interest;
e) determine elasticity parameters of regions between at least two of the tracking focal points at the same depth and on at least two adjacent tracking lines as a function of the displacements caused by the shear wave at the tracking focal points;
f) modify the appearance of at least one pixel of the B-mode image inside the said regions relatively to the grey-scale B-mode image as a function of at least one of the elasticity parameters determined for the said regions;
g) display the at least one pixel having the modified appearance at the corresponding pixel of the B-mode image;
wherein step f) comprises determining pixel appearance in the HSL (Hue, Saturation, Lightness) or the HSV (Hue, Saturation, Value) or the HSI (Hue, Saturation, Intensity) color three space coordinates; and
wherein the pixel appearance is set by encoding the B-mode intensity value into a first coordinate, the elasticity or velocity parameter into a second coordinate and a fixed value into a third coordinate of the color three space coordinates.

27. An ultrasound system for shear wave elasticity imaging (SWEI) comprising:
an ultrasound probe;
an ultrasound transmit wave generator and an ultrasound transmit beamformer to provide transmit signals to the ultrasound probe;
an ultrasound receive-beamformer;
ultrasound receive signals processing unit for generating ultrasound image data from received echo signals;
a shear wave excitation pulse generator and a shear wave beamformer;
an image display;
a memory storing program instructions; and
at least one processor that executes the program instructions to:
a) acquire B-mode ultrasound images of a target region in a body under examination;
b) select a region of interest inside the said B-mode image;
c) transmit a shear wave excitation pulse focalized on an excitation region;
d) measure displacements of a certain number of tracking focal points at different depths positions along each one of a predefined number of laterally staggered tracking lines within the selected region of interest;
e) determine elasticity parameters of the regions between at least two of the tracking focal points at the same depth and on at least two adjacent tracking lines as a function of the displacements caused by the shear wave at the said tracking focal points;
f) determine the statistical reliability of the velocity or of the elasticity parameter as calculated;
g) modify the appearance of at least one pixel of the B-mode image inside the said regions relatively to the grey-scale B-mode image as a function of the elasticity parameter and the statistical reliability of the elasticity parameter;
i) display the at least one pixel having the modified appearance at the corresponding pixel of the B-mode image.

28. A system according to claim 27, wherein when the at least one processor performs step g), the at least one processor determines pixel appearance in the HSL (Hue, Saturation, Lightness) or the HSV (Hue, Saturation, Value) or the HSI (Hue, Saturation, Intensity) color three space coordinates.

29. A system according to claim 28, wherein the at least one processor sets the pixel appearance by encoding the B-mode intensity value into a first coordinate, the elasticity or velocity parameter into a second coordinate and the statistical reliability of the elasticity parameter into a third coordinate of the color three space coordinates.

30. A system according to claim 29, wherein the at least one processor encodes the elasticity or velocity parameter to Hue coordinate, the at least one processor encodes the statistical reliability to Saturation coordinate, and the at least one processor encodes B-mode intensity values to the remaining color space coordinate.

31. A system according to claim 30, wherein the at least one processor sets a threshold value of statistical reliability of elasticity or velocity parameter, and the at least one processor sets a discrete value of the saturation such as 1 and 0, respectively, for a statistical reliance factor under and above the said threshold.

32. A system according to claim 27, wherein the at least one processor operates the image display such that the elasticity or velocity parameter and the statistical reliability of elasticity or velocity parameter are visualized as a single image and the corresponding B-mode image is visualized as another image placed beside the B-mode image.

* * * * *